(12) United States Patent
Wang et al.

(10) Patent No.: US 10,160,835 B2
(45) Date of Patent: Dec. 25, 2018

(54) SELF-HEALING POLYMERS AND APPLICATIONS THEREOF

(71) Applicants: The Board of Trustees of the Leland Stanford Junior University, Stanford, CA (US); Nanjing University, Nanjing, Jiangsu (CN)

(72) Inventors: Chao Wang, Stanford, CA (US); Cheng-Hui Li, Stanford, CA (US); Zhenan Bao, Stanford, CA (US)

(73) Assignees: The Board of Trustees of the Leland Stanford Junior University, Stanford, CA (US); Nanjing University, Nanjing (CN)

( * ) Notice: Subject to any disclaimer, the term of this patent is extended or adjusted under 35 U.S.C. 154(b) by 13 days.

(21) Appl. No.: 15/385,674

(22) Filed: Dec. 20, 2016

(65) Prior Publication Data

US 2017/0174842 A1    Jun. 22, 2017

Related U.S. Application Data

(60) Provisional application No. 62/270,841, filed on Dec. 22, 2015.

(51) Int. Cl.
*C08G 77/30* (2006.01)
*A61L 24/00* (2006.01)
*C08G 77/398* (2006.01)

(52) U.S. Cl.
CPC ........ *C08G 77/398* (2013.01); *A61L 24/0031* (2013.01)

(58) Field of Classification Search
CPC .................. C08G 77/398; A61L 24/0031
USPC ....................................... 524/403
See application file for complete search history.

(56) References Cited

U.S. PATENT DOCUMENTS

| | | | |
|---|---|---|---|
| 2009/0015272 A1* | 1/2009 | Jones | B32B 5/26 324/693 |
| 2012/0165432 A1* | 6/2012 | Bateman | C08G 59/502 523/461 |
| 2012/0208895 A1* | 8/2012 | Vittoria | A61K 6/08 514/772.3 |
| 2016/0049217 A1 | 2/2016 | Tee et al. | |

OTHER PUBLICATIONS

Mauldin et al. "Self-healing polymers and composites", International Material Reviews, (2010), vol. 55, No. 6, pp. 317-346, (Year: 2010).*
Balkenende, D.W.R. et al. (2014) "Mechanochemistry with Metallosupramolecular Polymers," J. Am. Chem. Soc. 136(29):10493-10498.
Basak, S. et al. (2014) "Multi-stimuli responsive self-healing metallohydrogels: tuning of the gel recovery property," Chem. Commun. (Camb.) 50(18):2356-2359.

(Continued)

*Primary Examiner* — Michael M Bernshteyn
(74) *Attorney, Agent, or Firm* — Foley & Lardner LLP; Cliff Z. Liu

(57) ABSTRACT

A self-healing polymer includes metal ions and a polymer network including polymer chains cross-linked through coordination bonds with the metal ions. Each polymer chain includes ligands within a backbone of the polymer chain, and the ligands include metal ion coordination sites.

12 Claims, 30 Drawing Sheets

(56) References Cited

OTHER PUBLICATIONS

Bode, S. et al. (2013) "Self-healing metallopolymers based on cadmium bis(terpyridine) complex containing polymer networks," Polym. Chem. 4:4966-4973.

Bode, S. et al. (2013) "Self-Healing Polymer Coatings Based on Crosslinked Metallosupramolecular Copolymers," Adv. Mater. 25:1634-1638.

Burnworth, M. et al. (2011) "Optically healable supramolecular polymers," Nature 472:334-337.

Chen, Y. et al. (2012) "Multiphase design of autonomic self-healing thermoplastic elastomers," Nature Chem. 4:467-472.

Cordier, P. et al. (2008) "Self-healing and thermoreversible rubber from supramolecular assembly," Nature 451(7181):977-980.

Holten-Andersen, N. et al. (2011) "pH-induced metal-ligand cross-links inspired by mussel yield self-healing polymer networks with near-covalent elastic moduli," PNAS 108(7):2651-2655.

Kersey, F.R. et al. (2007) "A hybrid polymer gel with controlled rates of cross-link rupture and self-repair," J Royal Soc. Interface 4(13):373-380.

Krogsgaard, M. et al. (2013) "Self-Healing Mussel-Inspired Multi-pH-Responsive Hydrogels," Biomacromolecules 14(2):297-301.

Li, C-H. et al. (2016) "A highly stretchable autonomous self-healing elastomer," Nature Chemistry 8:618-624.

Sandmann, B. et al. (2015) "The Self-Healing Potential of Triazole-Pyridine-Based Metallopolymers," Macromol. Rapid Commun. 36(7):604-609.

Tee, B.C-K. et al. (2012) "An electrically and mechanically self-healing composite with pressure- and flexion-sensitive properties for electronic skin applications," Nature Nanotech. 7:825-832.

Wang, C. et al. (2013) "A rapid and efficient self-healing thermo-reversible elastomer crosslinked with graphene oxide," Adv. Mater. 25(40):5785-5790.

Wang, Q. et al. (2010) "High-water-content mouldable hydrogels by mixing clay and a dendritic molecular binder," Nature 463:339-343.

Wang, Z. et al. (2013) "Facile UV-Healable Polyethylenimine-Copper (C2H5N-Cu) Supramolecular Polymer Networks," Polymer Chemistry 4(18):4897-4901.

White, S.R. et al. (2001) "Autonomic healing of polymer composites," Nature 409:794-797.

Williams, K.A. et al. (2007) "Towards electrically conductive, self-healing materials," J. Royal Soc. Interface 4(13):359-362.

Yang, B. et al. (2014) "Self-healing metallo-supramolecular polymers from a ligand macromolecule synthesized via copper-catalyzed azide-alkyne cycloaddition and thiol-ene double 'click' reactions," Polym. Chem. 5(6):1945-1953.

\* cited by examiner $^{13}$C NMR

SELF-HEALING POLYMERS AND APPLICATIONS THEREOF

CROSS-REFERENCE TO RELATED APPLICATION

This application claims the benefit of U.S. Provisional Application No. 62/270,841, filed Dec. 22, 2015, the content of which is incorporated herein by reference in its entirety.

STATEMENT REGARDING FEDERALLY SPONSORED RESEARCH OR DEVELOPMENT

This invention was made with Government support under contract FA9550-15-1-0106 awarded by Air Force Office of Scientific Research. The Government has certain rights in this invention.

BACKGROUND

The ability to autonomously repair inflicted damage, such as through self-healing, is an important survival feature of living creatures. Animal muscle is a biomaterial that has long fascinated the scientific world: it is strong, elastic and able to undergo self-healing when wounded. Synthetic polymers have been designed to self-heal by encapsulating healing agents or incorporating dynamic bonds. However, most of these approaches involve the input of energy (either heat or light) or the assistance of a liquid monomer and a catalyst, solvents or plasticizers. Autonomous self-healing rubbers, which are typically based on moisture-sensitive hydrogen bonding, can lack stability against moisture. An improved self-healing chemistry that will afford ambient temperature, autonomous, repeatable self-healing ability, along with extended environmental stability, is highly desirable.

It is against this background that a need arose to develop the self-healing polymers of embodiments of this disclosure.

SUMMARY

Biological muscles are strong, elastic and capable of self-healing. Synthetic materials possessing these properties are highly desirable; however, realizing these properties remains challenging. Herein some embodiments are directed to a polymer network cross-linked by a metal-ligand design to successfully achieve simultaneously ultra-high stretchability (e.g., up to about 45 times of reversible deformation with a high cross-linking density and about 100 times of irreversible deformation with a lower cross-linking density) with high dielectric strength, autonomous self-healing and the capability of mechanical actuation. The healing process can take place at a temperature as low as about −20° C. (or lower) and is not significantly affected by surface aging and moisture. The metal-ligand coordination system of some embodiments, namely Fe(III) and 2,6-pyridinedicarboxamide, is designed to possess both strong pyridyl-Fe$^{III}$ and weaker carboxamido-Fe$^{III}$ interaction sites in a single ligand. As a result, the Fe(III)-2,6-pyridinedicarboxamide bonds can readily break and reform. The super-stretchability of the polymer can be the result of chain unfolding and sliding during stretching. On the other hand the polymer can partially recover to its original length upon unloading with the recoverability decreasing with strain. Moreover, the dynamic rupture and reconstruction of Fe(III)-2,6-pyridinedicarboxamide coordination complexes and the high poly (dimethylsiloxane) (PDMS) polymer chain mobility lead to autonomous self-healing of the material.

In some embodiments, a self-healing polymer includes metal ions and a polymer network including polymer chains cross-linked through coordination bonds with the metal ions, wherein each polymer chain includes ligands within a backbone of the polymer chain, and the ligands include metal ion coordination sites.

In some embodiments, at least one of the ligands is a poly-dentate ligand including multiple metal ion coordination sites having different bonding strengths.

In some embodiments, the metal ions are selected from transition metal ions and metal ions of lanthanides.

In some embodiments, at least one of the ligands is a poly-dentate ligand, the poly-dentate ligand includes a first metal ion coordination site having a first bonding strength, a second metal ion coordination site having a second bonding strength, and a third metal ion coordination site having a third bonding strength, and the first bonding strength, the second bonding strength, and the third bonding strength are different.

In some embodiments, the first metal ion coordination site includes i) a nitrogen atom of a heteroaryl group or ii) a carboxylic acid group.

In some embodiments, the second metal ion coordination site includes a nitrogen atom of an amide group.

In some embodiments, the third metal ion coordination site includes an oxygen atom of an amide group.

In some embodiments, each polymer chain further includes a moiety selected from a polysiloxane chain, a polyamide chain, a polyisobutene chain, a polyolefin chain, a polyester chain, and a polyurethane chain.

In some embodiments, each polymer chain is represented as $[M-L]_m$, where L is a ligand, M includes a moiety selected from, for example, a polysiloxane chain, a polyamide chain, a polyisobutene chain, a polyolefin chain, a polyester chain, and a polyurethane chain, and m is an integer greater than 1, such as 3 or greater, 5 or greater, 10 or greater, 15 or greater, 20 or greater, 50 or greater, or 100 or greater. M and L can be bonded via a linker moiety, such as —O—, a moiety including 1-3 carbon atoms, and so forth.

In some embodiments, the self-healing polymer has a glass transition temperature no greater than about 25° C.

In some embodiments, the glass transition temperature is a range from about −150° C. to about 25° C.

In some embodiments, the self-healing polymer has a reversible elongation of at least about 15× of an original length.

In some embodiments, a molar ratio of the poly-dentate ligand to the metal ions is in a range from about 1:10 to about 10:1, such as about 1:10 to about 1:1 or about 1:1 to about 10:1.

In some embodiments, an actuator includes a first electrode, a second electrode, and an elastomeric film connected to the first electrode and the second electrode. The elastomeric film includes metal ions and a polymer network including polymer chains cross-linked through coordination bonds with the metal ions, wherein each polymer chain includes a poly-dentate ligand including multiple metal ion coordination sites having different bonding strengths.

In some embodiments, the metal ions are selected from $Zn^{2+}$, $Fe^{2+}$, $Fe^{3+}$, $Co^{3+}$, and $Eu^{3+}$.

In some embodiments, the poly-dentate ligand includes at least one of a heteroaryl group, a carboxylic acid group, or an amide group.

In some embodiments, the elastomeric film has a dielectric constant of at least about 5.

In some embodiments, the elastomeric film has a dielectric strength of at least about 15 MV/m.

Other aspects and embodiments of this disclosure are also contemplated. The foregoing summary and the following detailed description are not meant to restrict this disclosure to any particular embodiment but are merely meant to describe some embodiments of this disclosure.

BRIEF DESCRIPTION OF THE DRAWINGS

For a better understanding of the nature and objects of some embodiments of this disclosure, reference should be made to the following detailed description taken in conjunction with the accompanying drawings.

d, Normalized UV-Vis spectra of (Et$_4$N)[Fe(Bupdca)$_2$] in different solvents, indicating that the complex is stable in these solvents.

Figure 13:
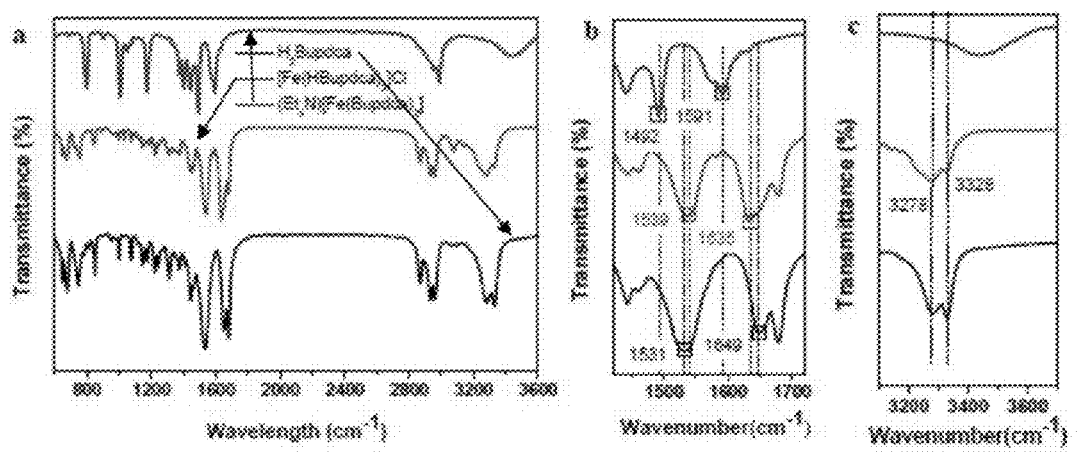

FIG. 13. FT-IR spectra of H$_2$Bupdca (bottom line), (Et$_4$N)[Fe(Bupdca)$_2$] (top line) and [Fe(HBupdca)$_2$]Cl (middle line) in the range of 500-3600 cm$^{-1}$. (a), 1420-1720 cm$^{-1}$ (b) and 3200-3500 cm$^{-1}$ (c). For (Et$_4$N)[Fe(Bupdca)$_2$], the N—H stretching at about 3278 and about 3328 cm$^{-1}$ disappeared, the amide I band at about 1649 cm$^{-1}$ and amide II band at about 1531 cm$^{-1}$ shifted to about 1591 cm$^{-1}$ and about 1492 cm$^{-1}$, respectively, in good agreement with the formation of full-deprotonated ligands and a [Fe(Bupdca)$_2$]$^-$ complex. For [Fe(HBupdca)$_2$]Cl, the N—H stretching at about 3278 and about 3328 cm$^{-1}$ can still be observed, but the intensity of peaks at about 3278 and about 3328 cm$^{-1}$ for ligand and Fe$^{3+}$ complex are different. The amide I band was shifted to a lower wavenumber at about 1635 cm$^{-1}$ while the amide II band was shifted to a higher wavenumber at about 1539 cm$^{-1}$, indicating that they are involved in coordination.

Figure 14:
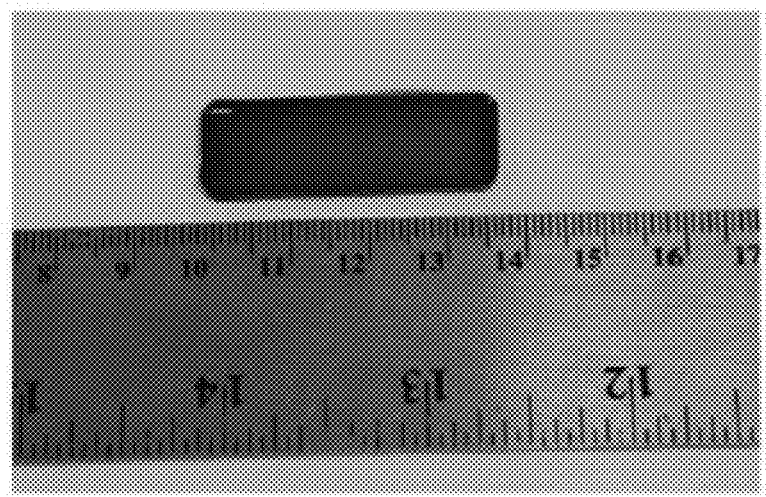

FIG. 14. Image of Fe-Hdpca-PDMS film (with a H$_2$pdca-PDMS ligand to Fe(III) metal molar ratio of about 1:2).

Figure 15:
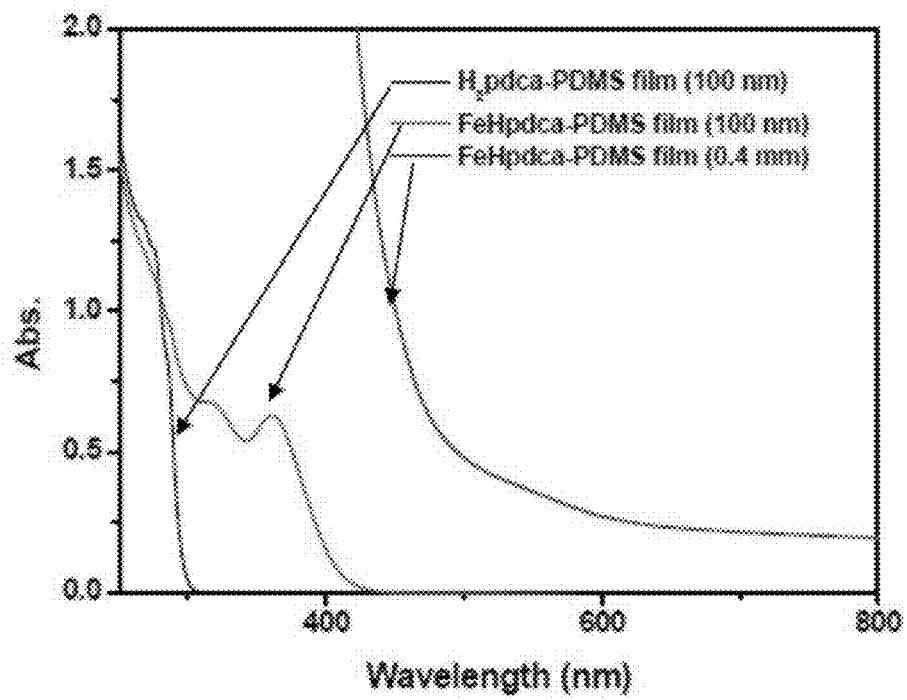

FIG. 15. UV-Vis spectra of H$_2$pdca-PDMS (with thickness of about 100 nm) and Fe-Hpdca-PDMS polymer (with thickness of about 100 nm and about 0.4 mm, respectively). The H$_2$pdca-PDMS ligand to Fe(III) metal molar ratio for the Fe-Hpdca-PDMS film is about 1:2. The about 100 nm films were prepared through spin coating on silica substrate while the about 0.4 mm film was prepared from solution casting in PTFE molds. The UV-Vis spectrum of H$_2$pdca-PDMS has a shoulder band at about 268 nm with two vibronic shoulders at about 276 and about 285 nm, respectively, assignable to the π-π transitions within the pyridine ring and C=O double bond. Upon complexation with Fe(III), this band appeared as a new single shoulder peak at about 280 nm. Moreover, a new band at about 315 nm and about 362 nm was observed which can be assigned to ligand-to-metal charge transfer (LMCT). The long wavelength tail at λ>about 400 nm in the UV-Vis spectrum, which is more significant in thick films, should be due to the presence of low energy absorbing Fe(III) complexes. Therefore, the resulting polymer network likely includes a mixture of various complexation structures.

Figure 16:
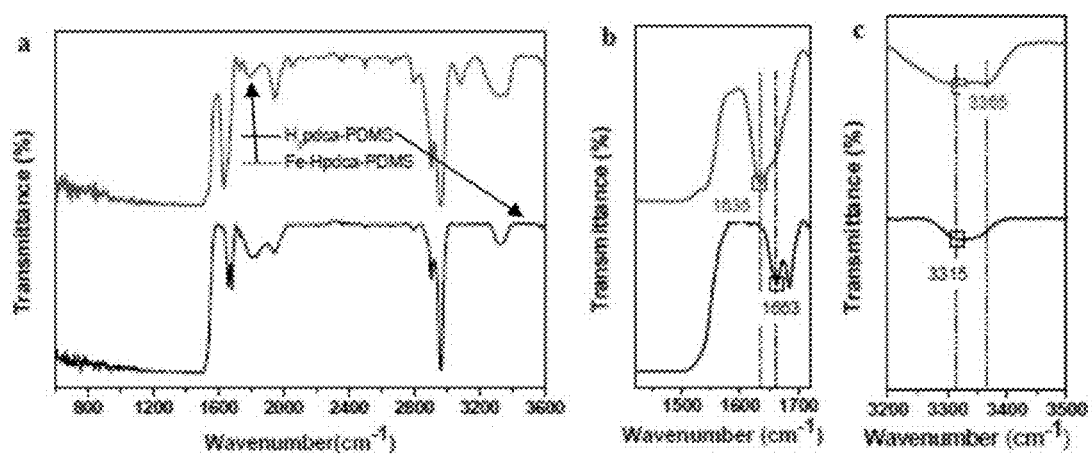

FIG. 16. FT-IR spectra of H$_2$pdca-PDMS (bottom line) and Fe-Hpdca-PDMS polymer (top line) in the range of 500-3600 cm$^{-1}$ (a), 1420-1720 cm$^{-1}$ (b) and 3200-3500 cm$^{-1}$ (c). The H$_2$pdca-PDMS ligand to Fe(III) metal molar ratio for the Fe-Hpdca-PDMS film is about 1:2. The FT-IR spectrum revealed that the amide I (C=O stretching) band shifted to lower wavenumbers upon coordination.

Figure 17:
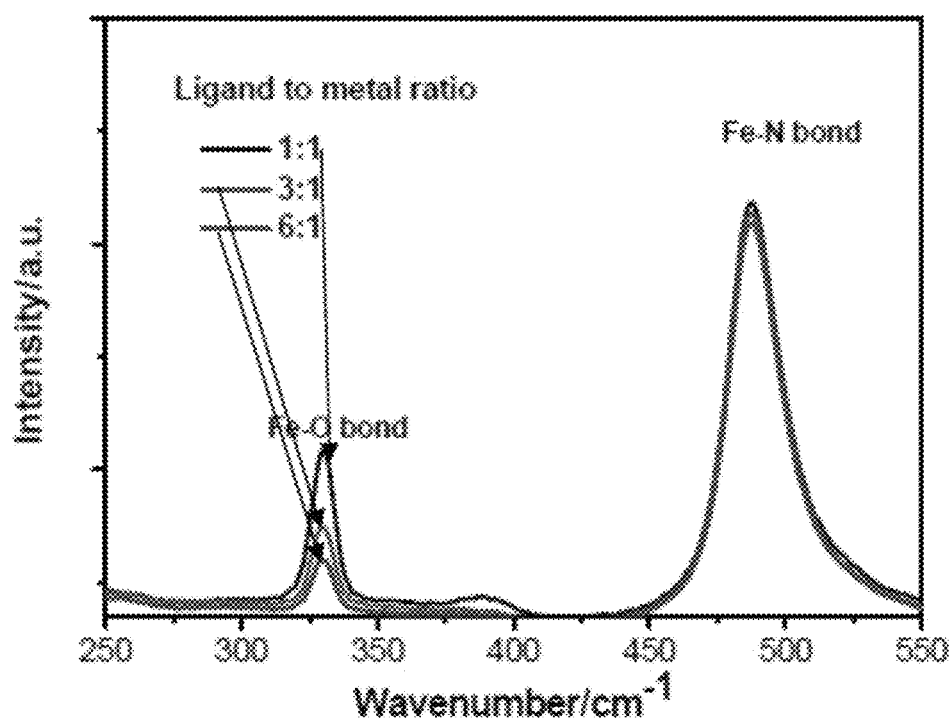

FIG. 17. Raman spectra of Fe-Hpdca-PDMS polymer with different Fe(III) ion to pdca ligand molar ratio. Both Fe—N and Fe—O coordination bonds are present in the as prepared polymer. The percentage of Fe—O coordination bonds increased as the Fe(III) ion to H$_2$pdca ligand molar ratio increases.

Figure 18:
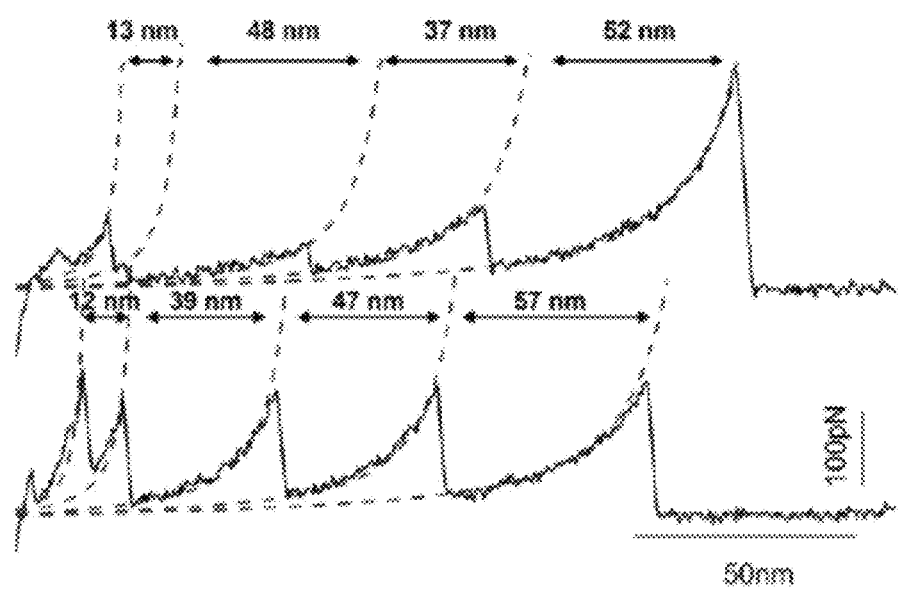

FIG. 18. The contour length increment (ΔLc) of Fe-Hpdca-PDMS derived from single-molecule (single chain) force spectroscopy measurement.

Figure 19:
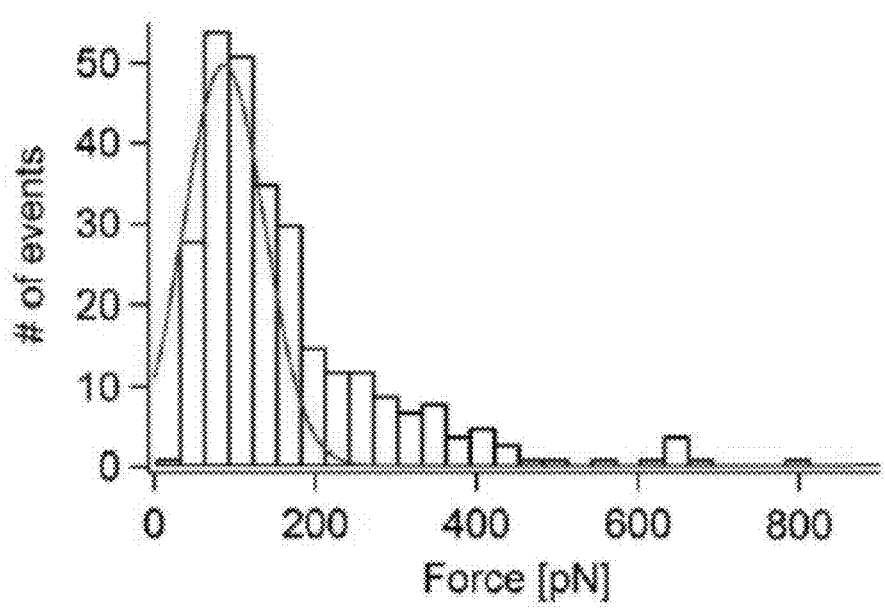

FIG. 19. Histogram (n=558) of the rupture forces of the Fe[(Hpdca)$_2$]$^+$ coordination complexes.

Figure 20:
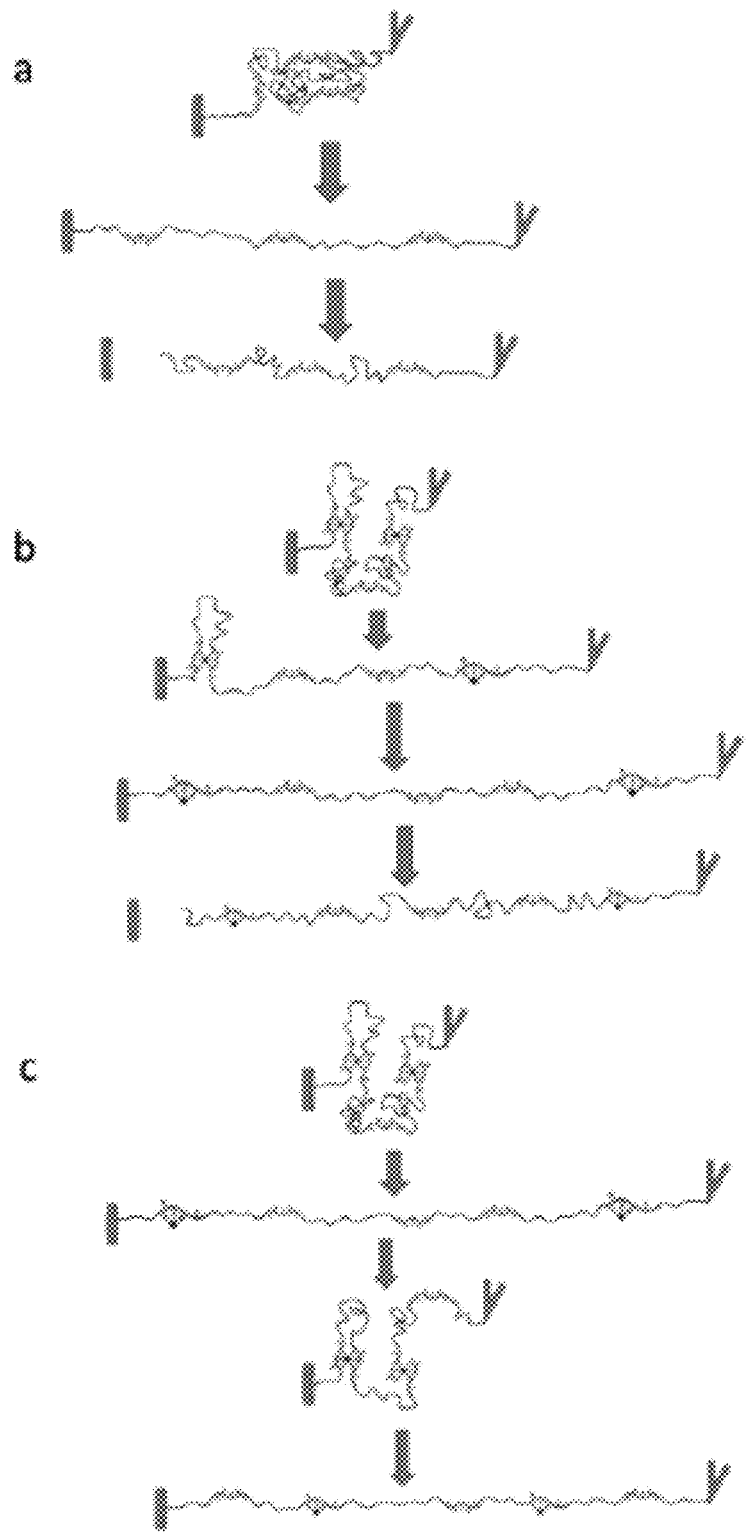

FIG. 20. The structure change of H$_2$pdca-PDMS and Fe-Hpdca-PDMS during single-molecule (single chain) force spectroscopy measurement. For H$_2$pdca-PDMS, the molecule was elongated due to stretching until it detached from the substrate (FIG. 20a). For Fe-Hpdca-PDMS, the molecule was elongated upon stretching accompanied by rupture of the [Fe(Hpdca)$_2$]$^+$ coordination complex (FIG. 20b), while the iron remain bound to one Hpdca motif, resulting in a meta-stable [Fe(Hpdca)]$^{2+}$ intermediate. The macromolecule can then collapse upon releasing, where the other Hpdca can chelate [Fe(Hpdca)]$^{2+}$ to form the [Fe(Hpdca)$_2$]$^+$ center, initiating the complete refolding of Fe-Hpdca-PDMS (FIG. 20c).

Figure 21:
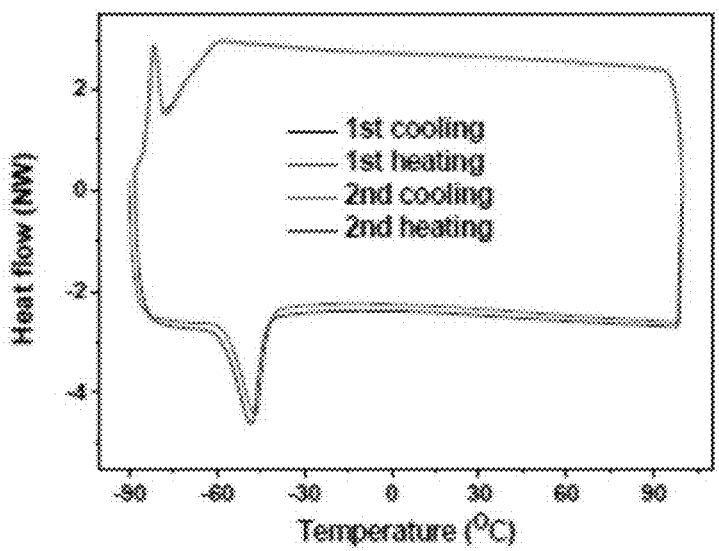

FIG. 21. DSC curves of Fe-Hpdca-PDMS polymer (with the H$_2$pdca-PDMS ligand to Fe(III) metal molar ratio of about 1:2). The exothermal peak at about −65.3° C. and endothermic peak at about −38.8° C. corresponded to the crystallization and melting, respectively. The T$_g$ should be below about 90° C. as there is no other exothermal/endothermal signal between the crystallization point and the lowest measurable temperature of the instrument.

Figure 22:
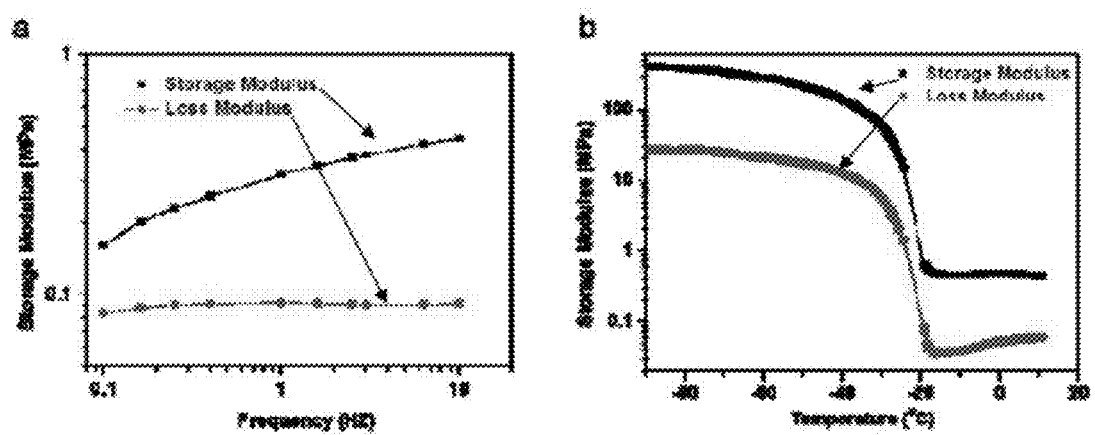

FIG. 22. Dynamic mechanical analysis result of the Fe-Hpdca-PDMS polymer (with the H$_2$pdca-PDMS ligand to Fe(III) metal molar ratio of about 1:2. a. Frequency sweeping shows that the storage modulus is higher than loss modulus at most frequencies. b. Temperature sweeping of the polymer sample.

Figure 23:
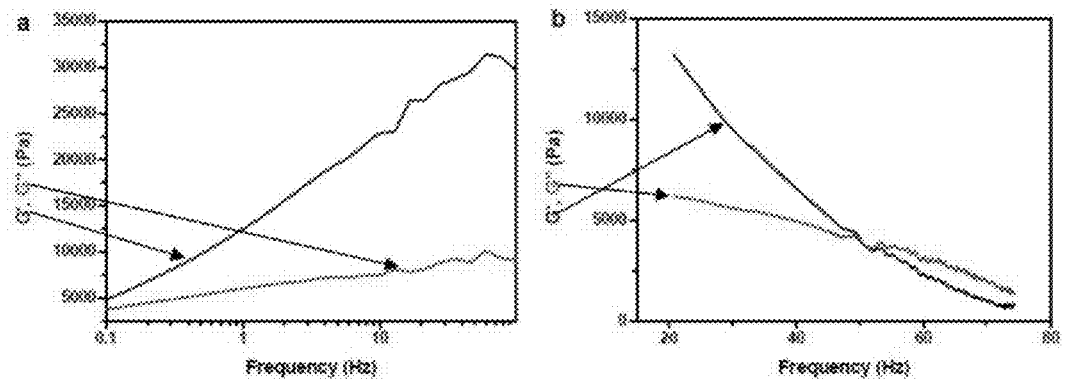

FIG. 23. Rheological test of Fe-Hpdca-PDMS polymer (with the H$_2$pdca-PDMS ligand to Fe(III) metal molar ratio of about 1:2). a. Loss modulus (G") and storage modulus (G') versus frequency at about 20° C.; b, Loss modulus (G") and storage modulus (G') versus temperature at about 1 Hz.

Figure 24:
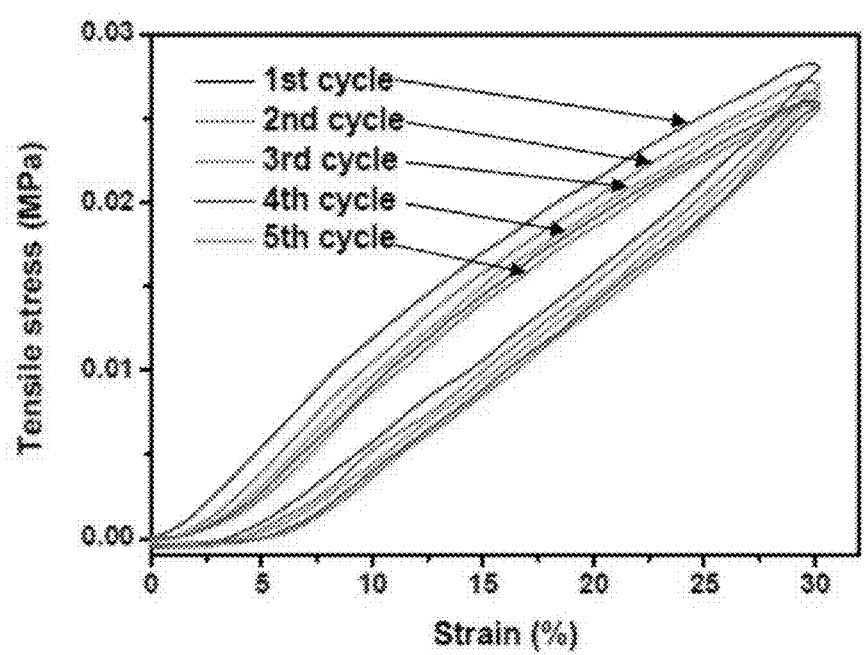

FIG. 24. Stress-strain curve of a film (with the H$_2$pdca-PDMS ligand to Fe(III) metal molar ratio of about 1:2) in cyclic stress-strain tests (about 30% strain) in successive stretching. Sample width: about 14 mm; Thickness: about 1 mm; Gage length: about 2 mm; Stretching speed: about 10 mm min$^{-1}$.

Figure 25:
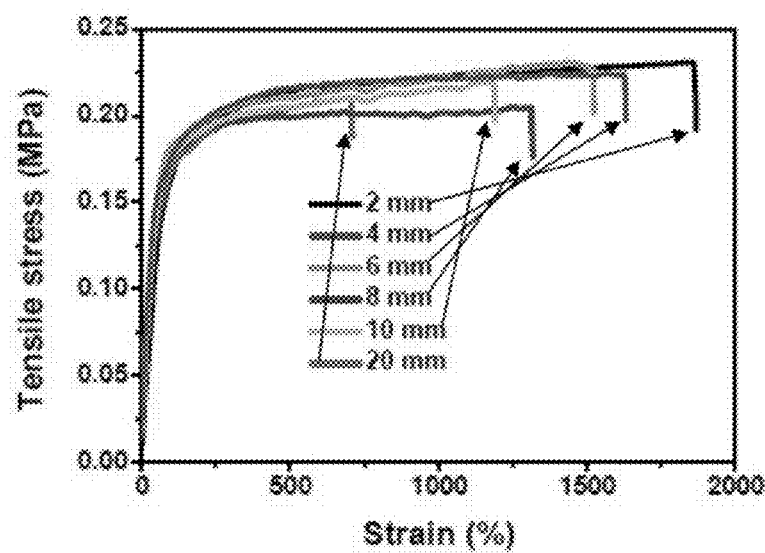

FIG. 25. Stress-strain curve of a film (with the H$_2$pdca-PDMS ligand to Fe(III) metal molar ratio of about 1:2) with different gage length. Sample width: about 14 mm; Thickness: about 1 mm; Stretching speed: about 10 mm min$^{-1}$.

Figure 26:
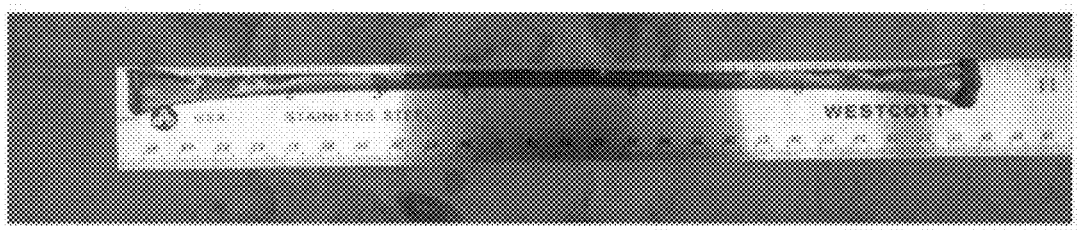

FIG. 26. Image of Fe-Hpdca-PDMS film with the molar ratio of Fe(III) metal to H$_2$pdca-PDMS ligand of about 1:6. After stretched to about 10000% strain and released for about 12 h, the film was about 25 cm in length, which is about 1000% of its original length, indicating that the stretched film was partially recoverable.

Figure 27:
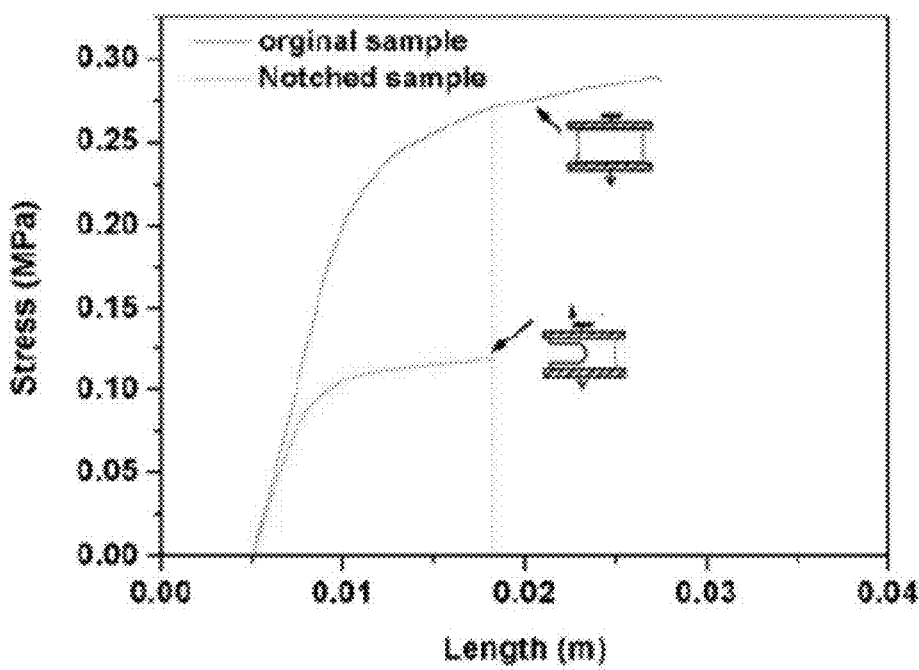

FIG. 27. Fracture test of the H$_2$pdca-PDMS polymer (with the H$_2$pdca-PDMS ligand to Fe(III) metal molar ratio of about 1:2). The sample size is about 25 mm in length with a gage width of about 5 mm and notch size of about 12.5 mm. The experiment was done by making a notch at the middle part of the sample and measuring the stress during the stretching process.

Figure 28:
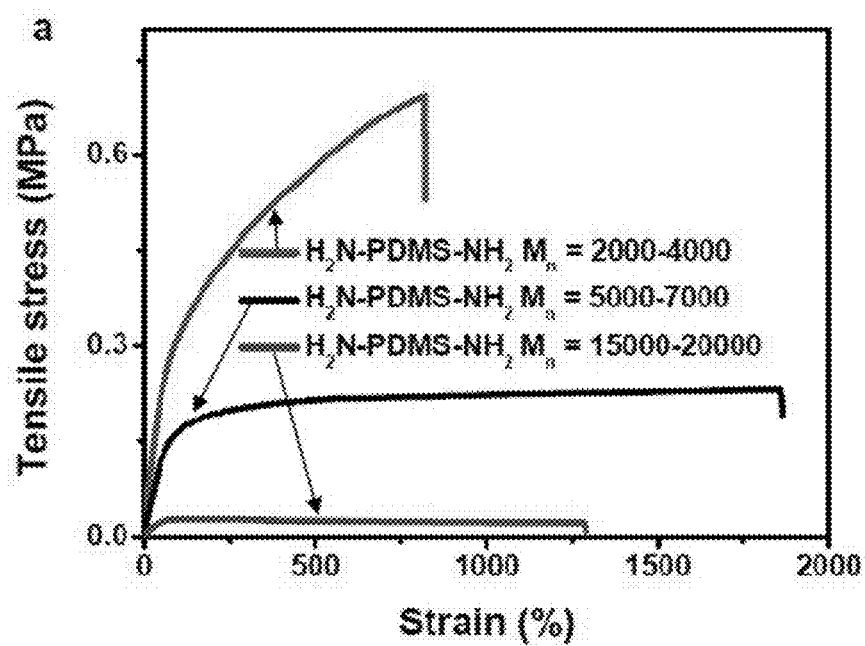

FIG. 28. Tensile stress curves of Fe-Hpdca-PDMS film (with the H$_2$pdca-PDMS ligand to Fe(III) metal molar ratio of about 1:2) with different density of metal-ligand interaction sites. Sample size: about 75×14×1.0 mm$^3$; Gage length: about 2 mm; Stretching speed: about 10 mm min$^{-1}$. The results show that the strength of the film is decreasing with the increasing of the percentage of Hpdca ligand, while the stretchability of the film from H$_2$N-PDMS-NH$_2$ with Mn of about 2500-4000 and about 15000-20000 are both poorer than that with Mn of about 5000-7000. The higher molecular weight H$_2$N-PDMS-NH$_2$ starting polymer leads to fewer amide binding sites and therefore poorer stretchability. The lower molecular weight H$_2$N-PDMS-NH$_2$ starting polymer can provide more amide binding sites, as evidenced by the increase of strength, but also show poorer stretchability due to shorter PDMS chains with constrained folding/unfolding ability.

Figure 29:
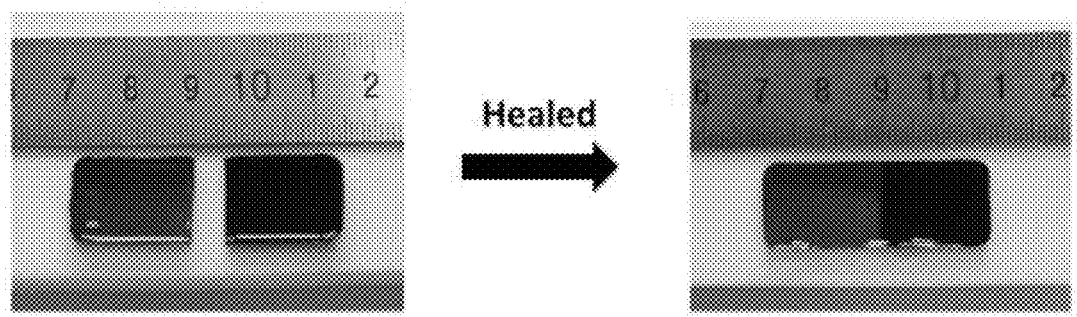

FIG. 29. Self-healing property of the Fe-Hpdca-PDMS film (with the H$_2$pdca-PDMS ligand to Fe(III) metal molar ratio of about 1:2).

Figure 30:
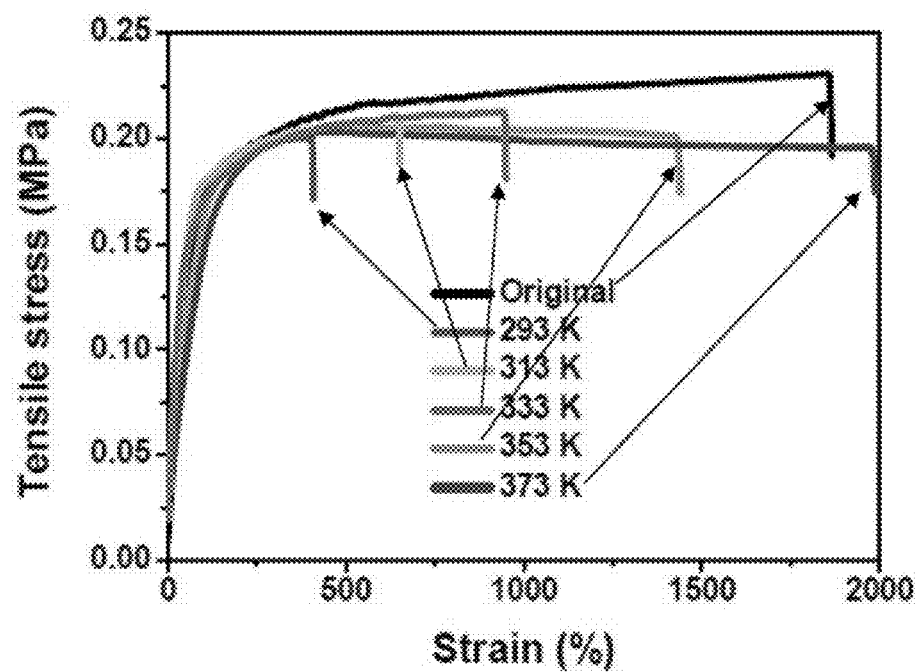

FIG. 30. Stress-strain curves of the film (with the H$_2$pdca-PDMS ligand to Fe(III) metal molar ratio of about 1:2) healed at different temperatures for about 4 h. Sample size: about 75×14×1.0 mm$^3$; Gage length: about 2 mm; Stretching speed: about 10 mm min$^{-1}$.

Figure 31:
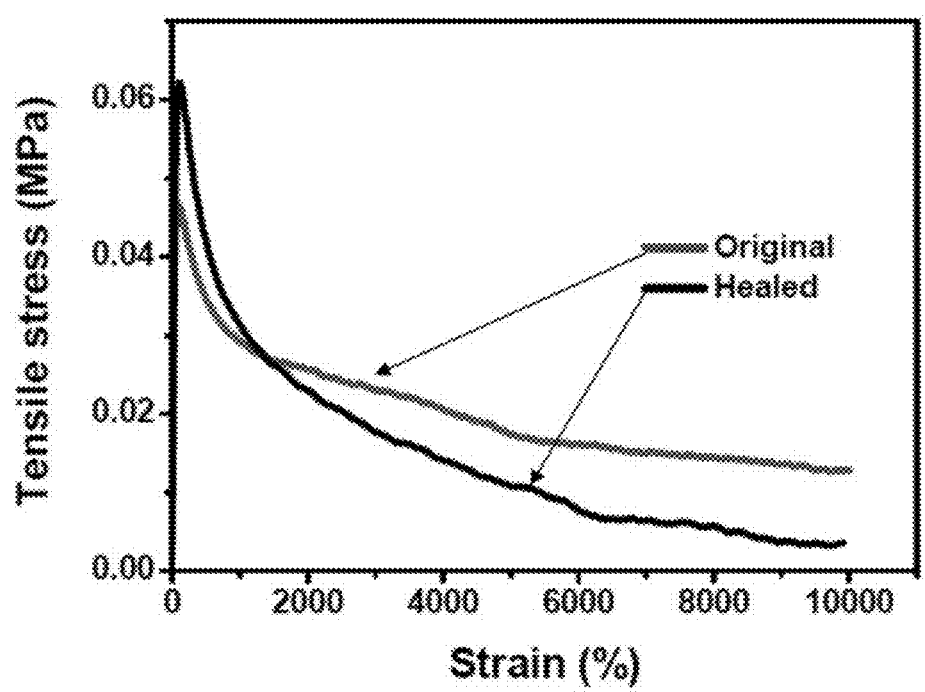

FIG. 31. Stress-strain curves of a film (with the molar ratio of Fe(III) metal to H$_2$pdca-PDMS ligand of about 1:6) healed at room temperature for about 12 h. Sample size: about 75×14×1.0 mm$^3$; Gage length: about 2 mm; Stretching speed: about 10 mm min$^{-1}$. The healing of this viscoelastic film is quick and efficient. The film healed at room temperature for about 12 h can be stretched to over about 100 times of its original length without breaking. As the film was very soft, the tensile stress data cannot be accurately determined with the instrument. The signal-to-noise ratio of the original tensile-strain curves was very low and therefore the stress-strain curves are smoothed.

Figure 32:
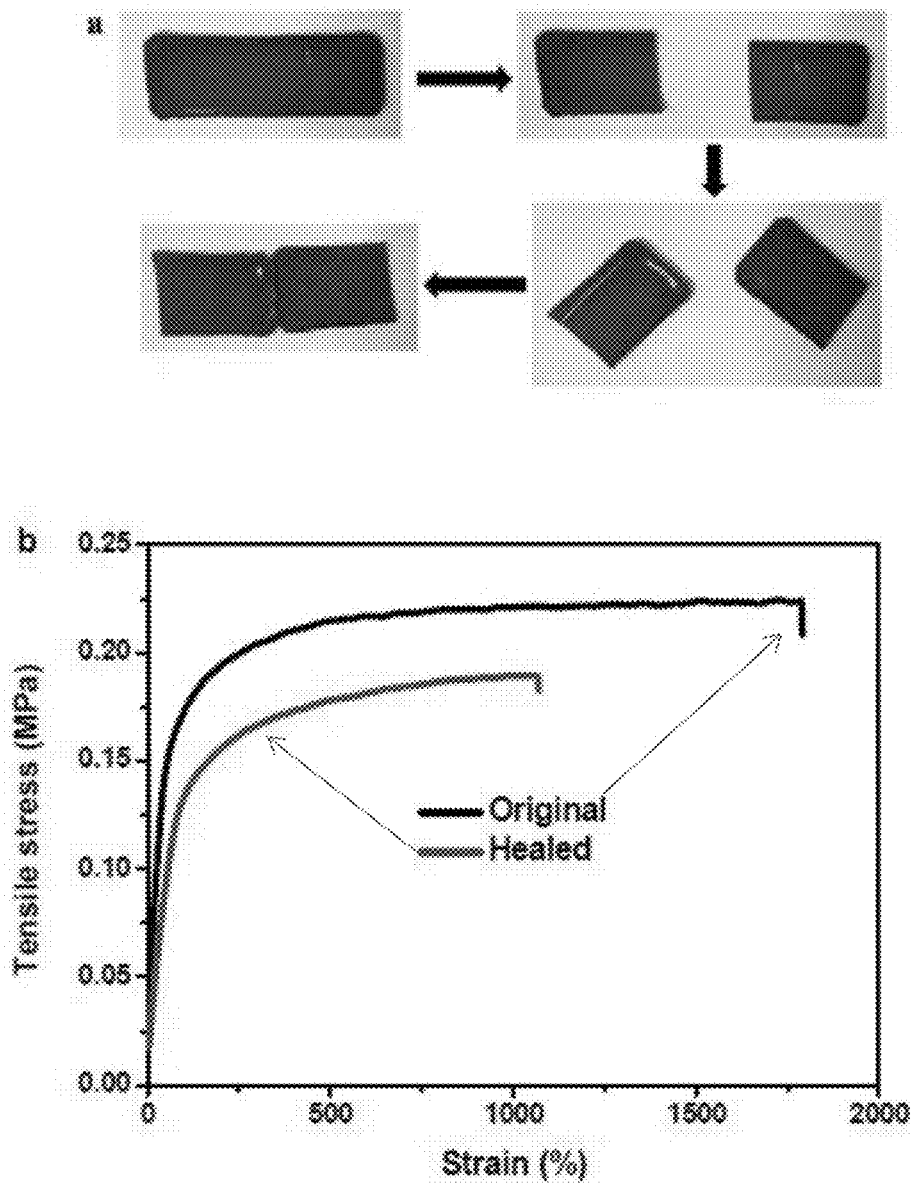

FIG. 32. Self-healing of Fe-pdca-PDMS film (with the H$_2$pdca-PDMS ligand to Fe(III) metal molar ratio of about 1:2) at undamaged surface. a, Image of procedures for self-healing from undamaged surface. b, The stress-strain curves of the film healed from undamaged surface at room temperature for about 24 h. Sample size: about 75×14×1.0 mm$^3$; Gage length: about 2 mm; Stretching speed: about 10 mm min$^{-1}$.

Figure 33:
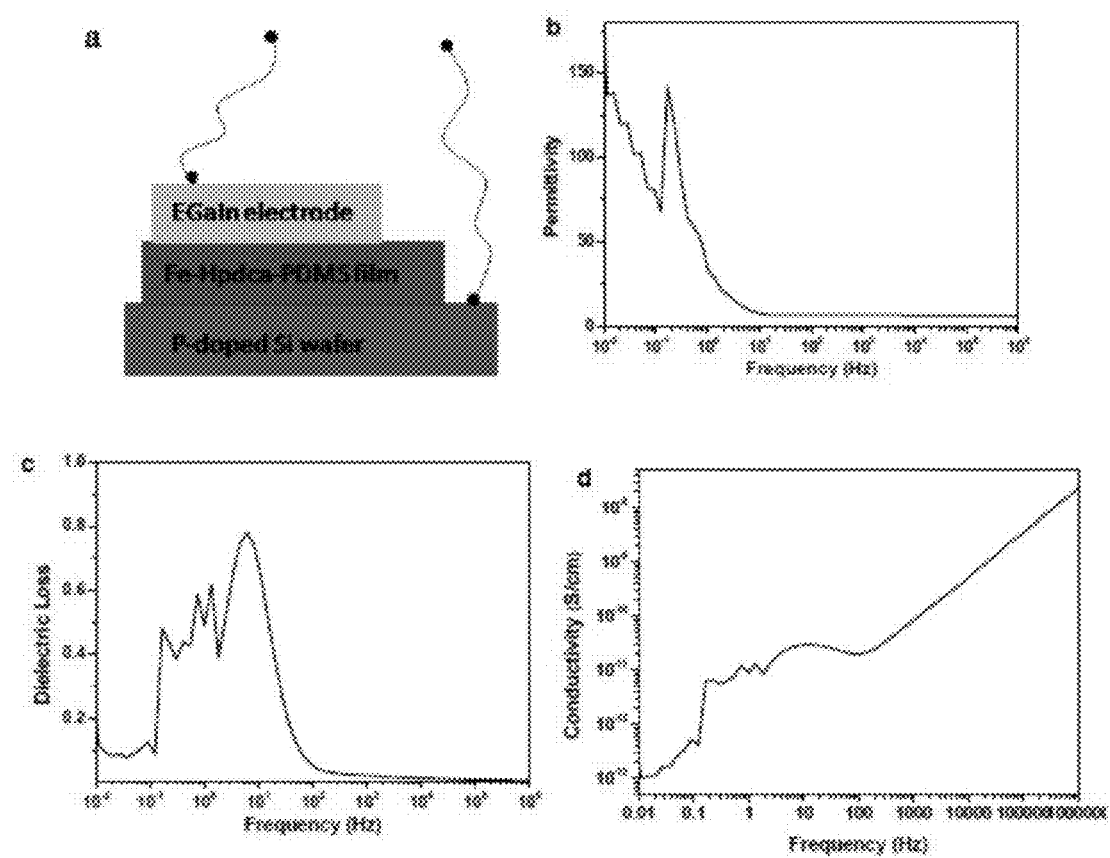

FIG. 33. Dielectric spectra of Fe-Hpdca-PDMS film (with the H$_2$pdca-PDMS ligand to Fe(III) metal molar ratio of about 1:2) from 0.01 Hz to 1 MHz. a, a device structure for the measurement. b, permittivity vs. frequency. c, dielectric loss vs. frequency. d, conductivity vs. frequency. The dielectric constant at low frequency is due to the movement of Cl$^-$ ions or residue solvent molecules in the polymer matrix.

Figure 34:
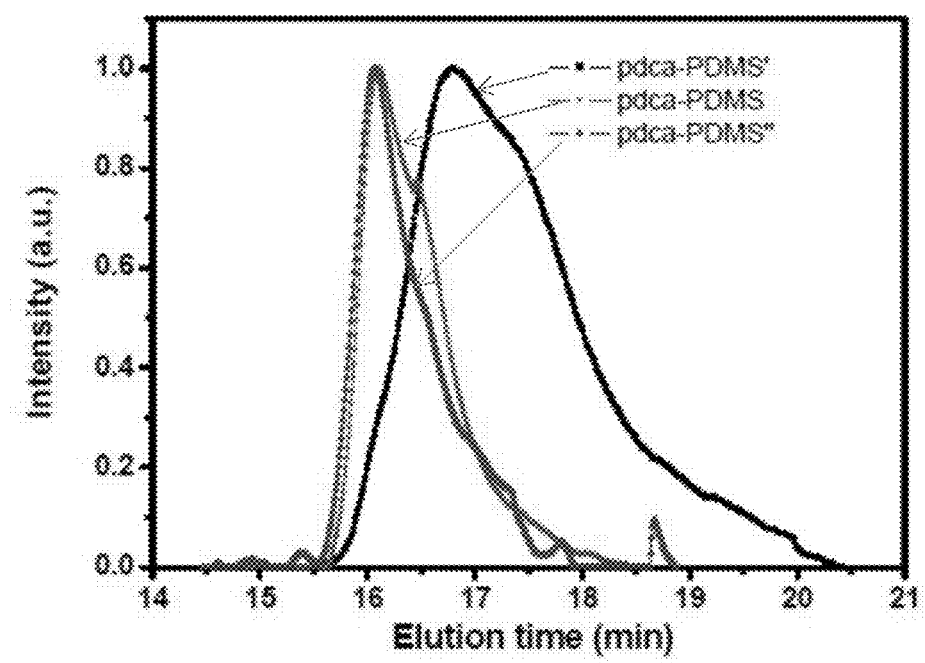

FIG. 34. GPC elution curves of H$_2$pdca-PDMS', H$_2$pdca-PDMS and H$_2$pdca-PDMS". Fe-Hpdca-PDMS, Fe-Hpdca-PDMS', and Fe-Hpdca-PDMS" were polymerized from H$_2$N-PDMS-NH$_2$ with Mn of about 5,000-7,000, about 2,500-4,000 and about 15,000-20,000, respectively.

Figure 35:
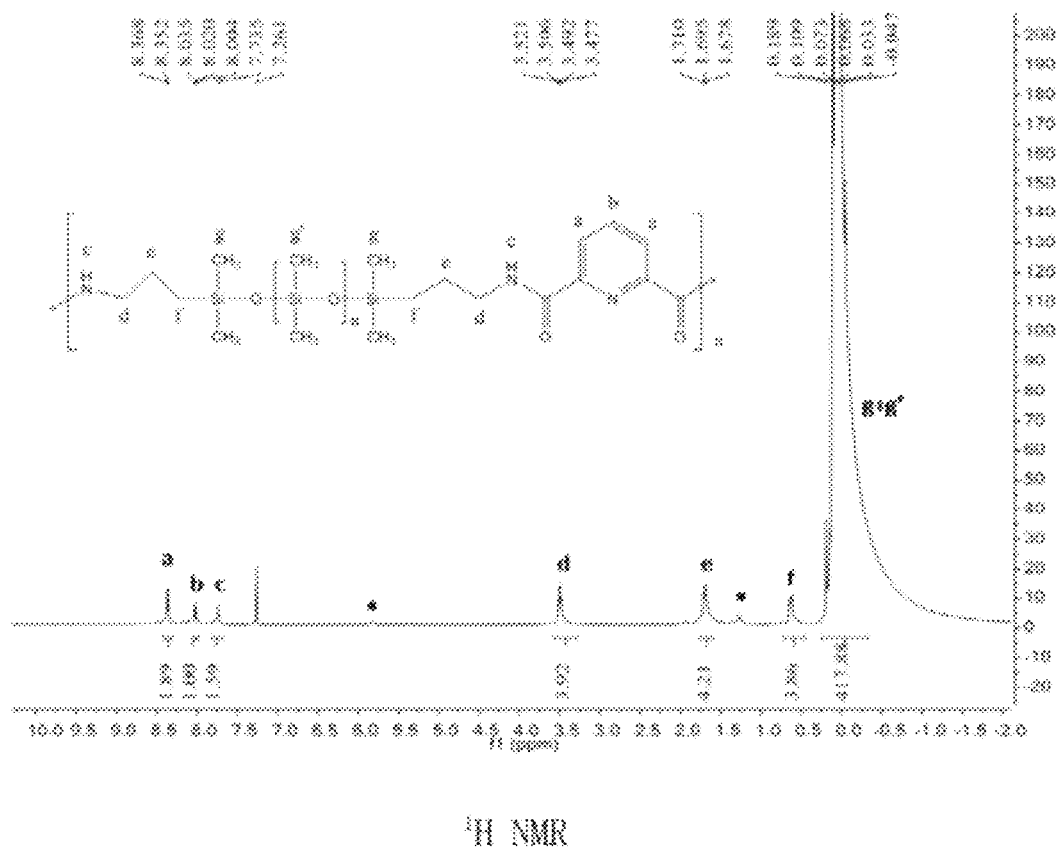
Figure 35:
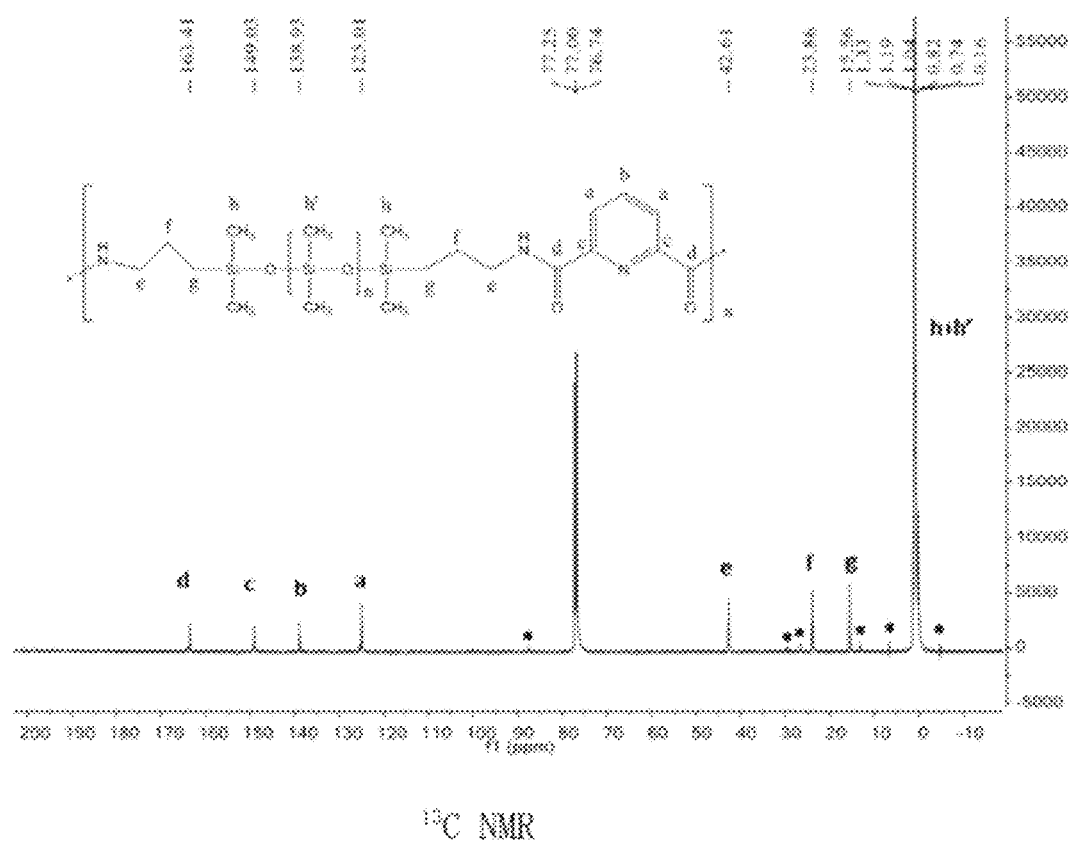

FIG. 35. $^1$H NMR and $^{13}$C NMR spectra of H$_2$dpca-PDMS polymer (synthesized from H$_2$N-PDMS-NH$_2$ with Mn of about 5000-7000). * indicates an impurity.

Figure 36:
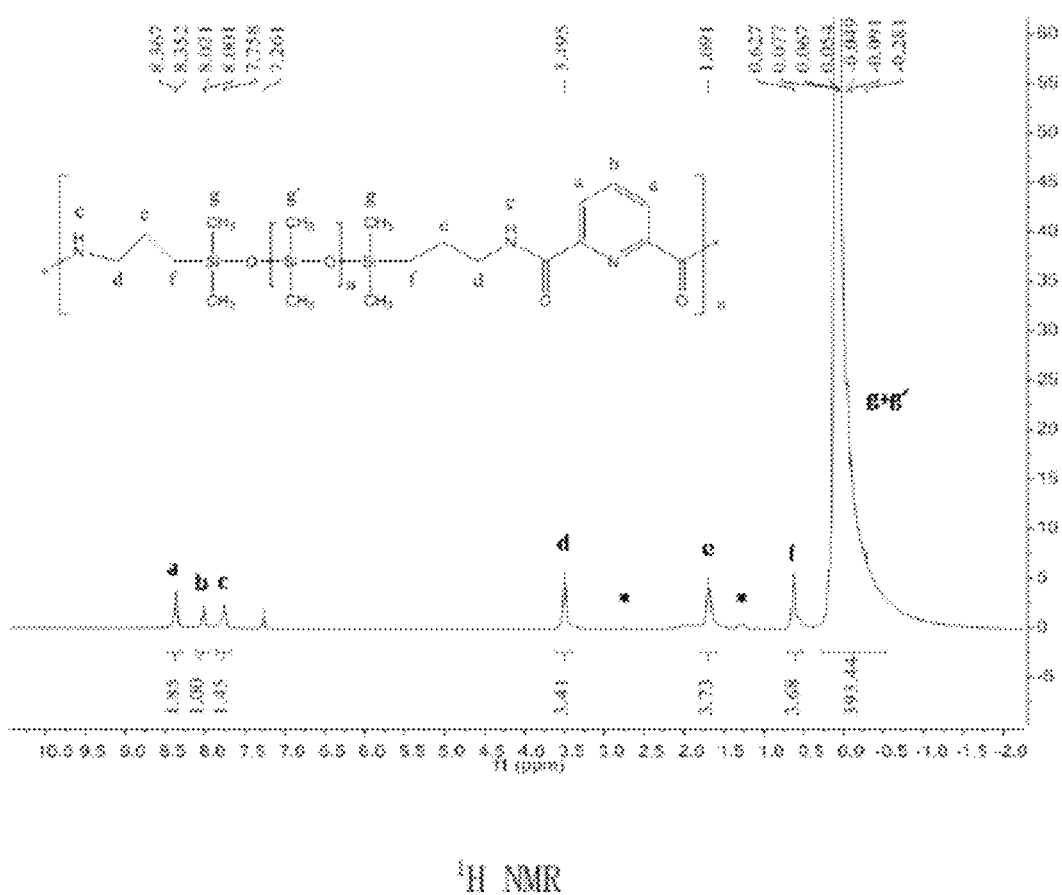
Figure 36:
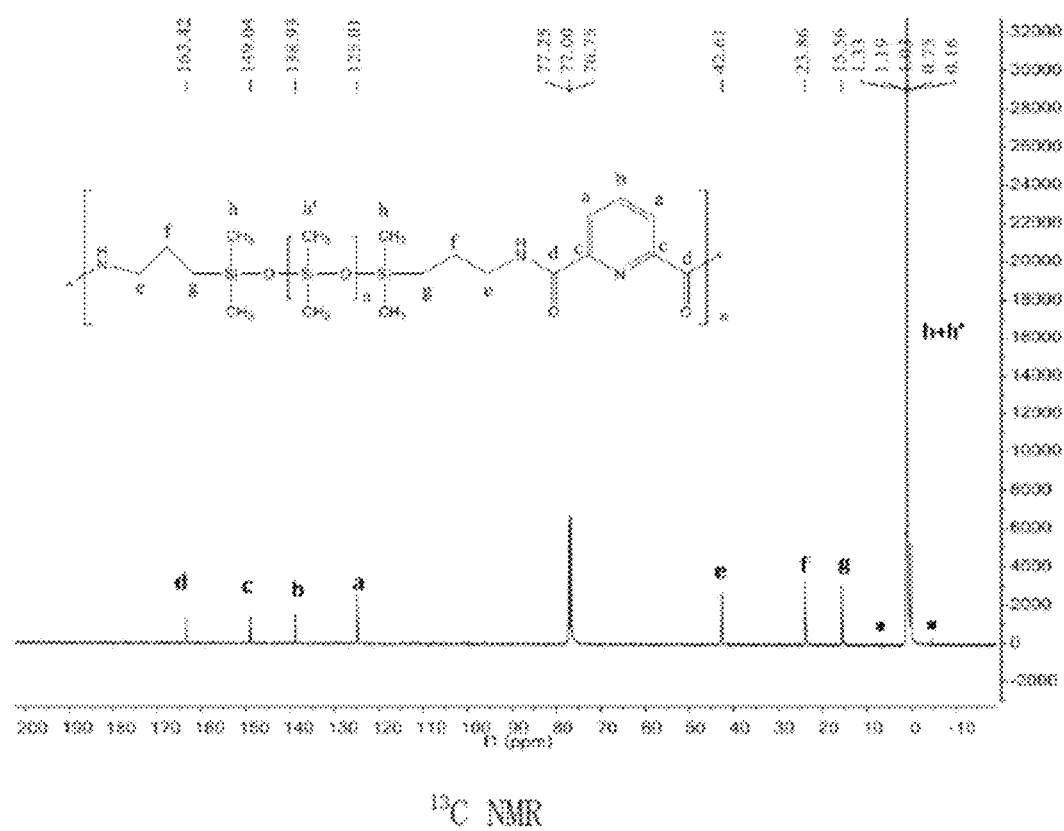

FIG. 36. $^1$H NMR and $^{13}$C NMR spectra of H$_2$dpca-PDMS' polymer (synthesized from H$_2$N-PDMS-NH$_2$ with Mn of about 2500-4000). * indicates an impurity.

Figure 37:
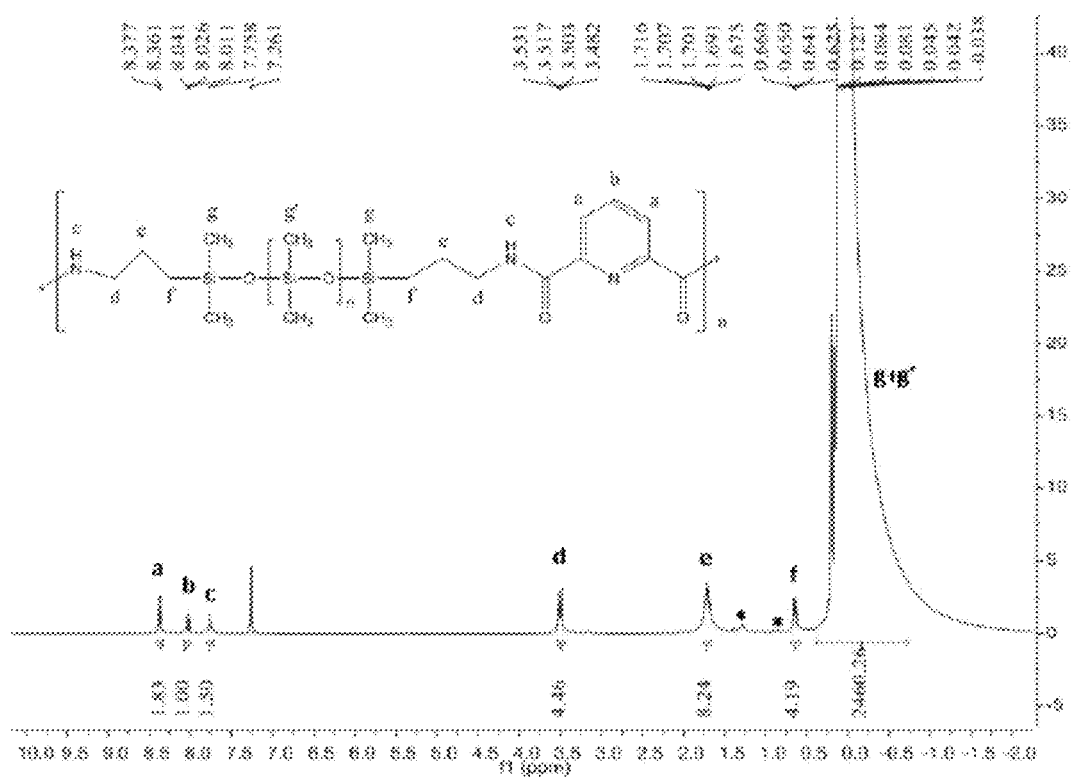
Figure 37:
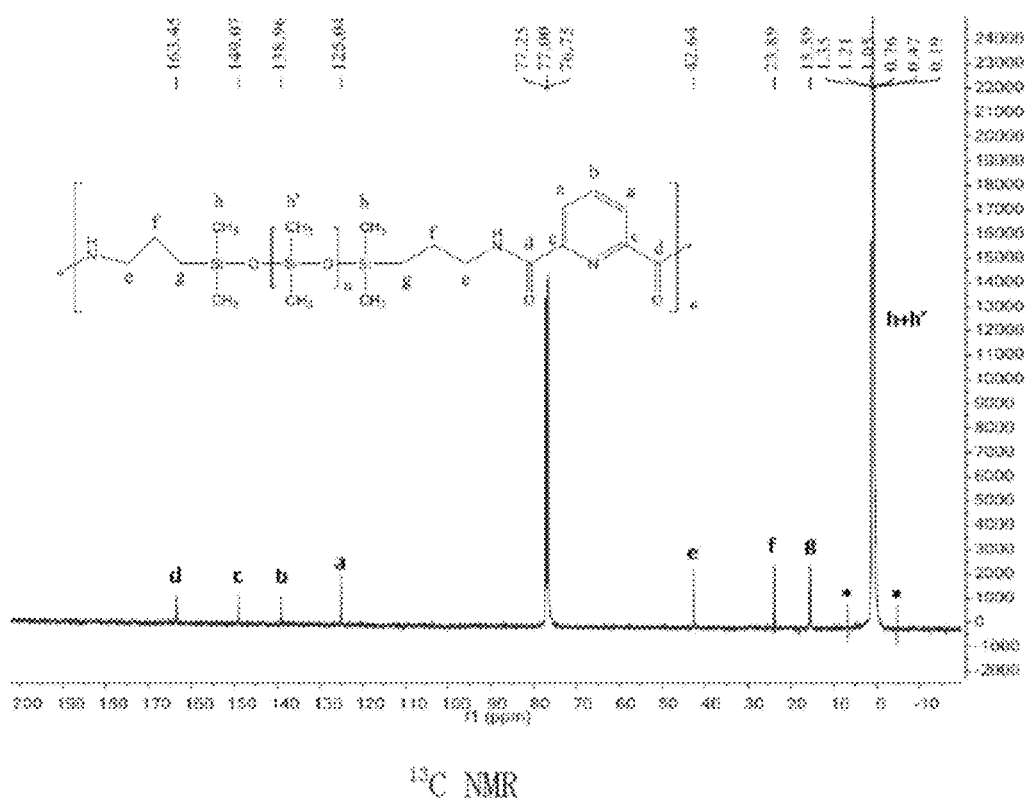

FIG. 37. $^1$H NMR and $^{13}$C NMR spectra of H$_2$dpca-PDMS" polymer (synthesized from H$_2$N-PDMS-NH$_2$ with Mn of about 15000-20000). * indicates an impurity.

DESCRIPTION

Self-Healing Polymers

Embodiments of this disclosure relate to self-healing polymers, composites formed of such self-healing polymers, and applications of such self-healing polymers and composites. In some embodiments, a self-healing polymer includes a cross-linked polymer network linked via a combination of strong and weak metal-ligand interactions. Upon damage of the polymer, the polymer self-heals without the need to apply external stimuli or the use of chemical agents to promote self-healing and damage repair. Advantageously, some embodiments of the polymer can demonstrate repeatable self-healing at a low temperature, along with high stretchability and high strength.

Some embodiments are directed to a design concept that takes advantage of the versatility in tuning the strength of metal-ligand interactions to achieve high strength, high stretchability and room temperature self-healing not susceptible to surface aging. Other approaches involving metal-ligand interactions for self-healing materials either rely on strong bonds, which involve external stimulus for healing, or used weak bonds, which could not provide sufficient mechanical strength. In order to have autonomous and reversible healing at room temperature, generally weak bonding strength, such as dynamic bond, is involved together with a low glass transition temperature ($T_g$) to afford polymer mobility. The design of some embodiments is to place strong metal-ligand binding sites adjacent to weak binding sites. As a result, the metal-ligand interactions are highly dynamic. They can readily break and reform, which is favorable for energy dissipation upon stretching and self-healing upon damaging, while the metal ions are still maintained near the ligands to allow rapid bond reformation. It is observed that the cooperative effect of these binding sites affords high stretchability and autonomous healing at room temperature. Here, some embodiments are directed to the design of a metal-ligand coordination system, which possesses both strong pyridyl-Fe$^{III}$ and weaker carboxamido-Fe$^{III}$ interaction sites in a single ligand, namely Fe(III) and 2,6-pyridinedicarboxamide. These ligands are incorporated into the backbones of highly flexible poly(dimethylsiloxane) (PDMS) polymers. A polymer network is obtained that shows simultaneously ultra-high stretchability and autonomous self-healing with good mechanical and dielectric strength. With this improved material in hand, its application toward self-healing artificial muscle actuators is demonstrated.

Material Design and Characterizations.

Figure 10:
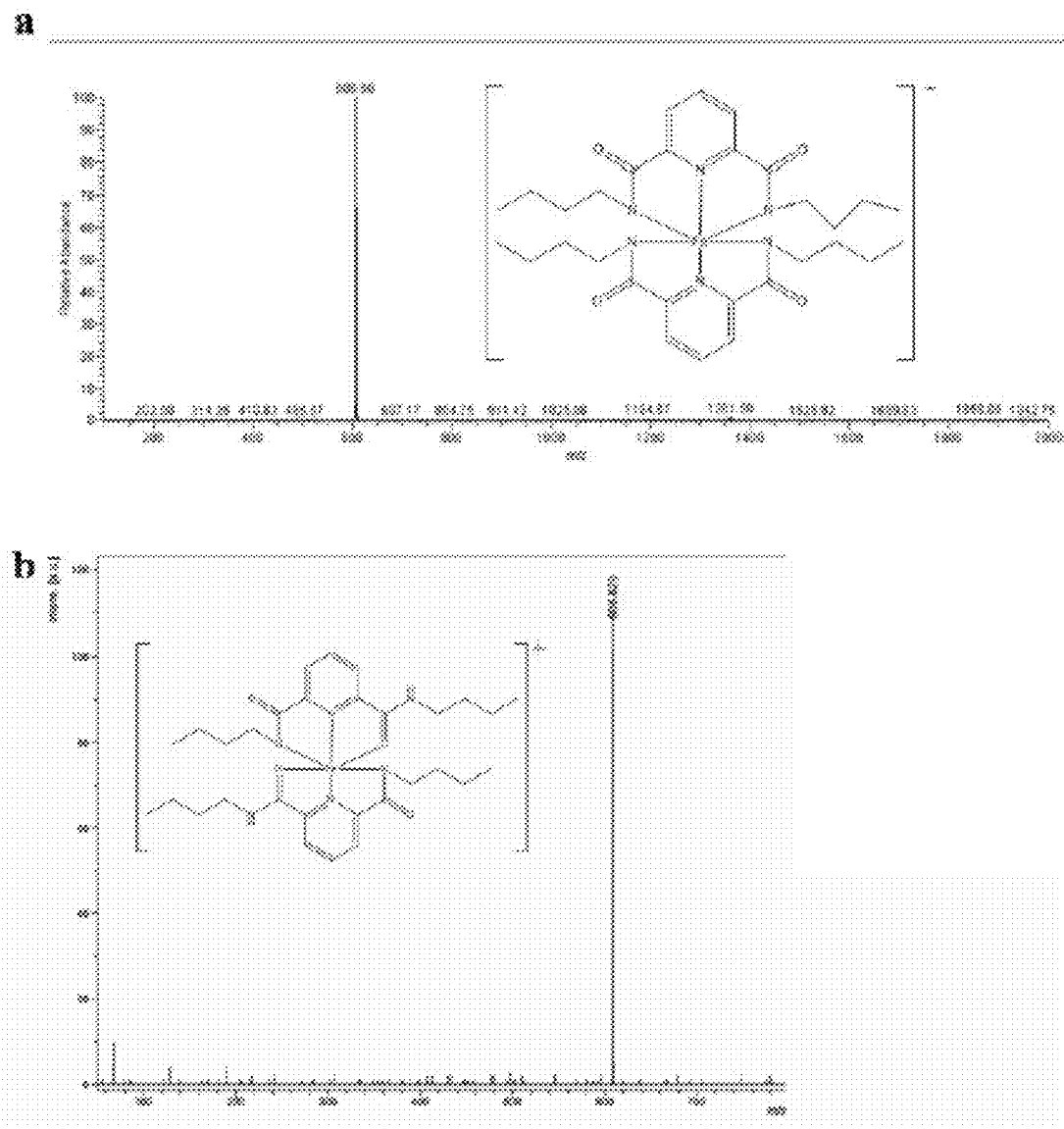
FIG. 10. Mass spectra of (a) $(Et_4N)[Fe(Bupdca)_2]$ and (b) $[Fe(HBupdca)_2]Cl$.
Figure 11:
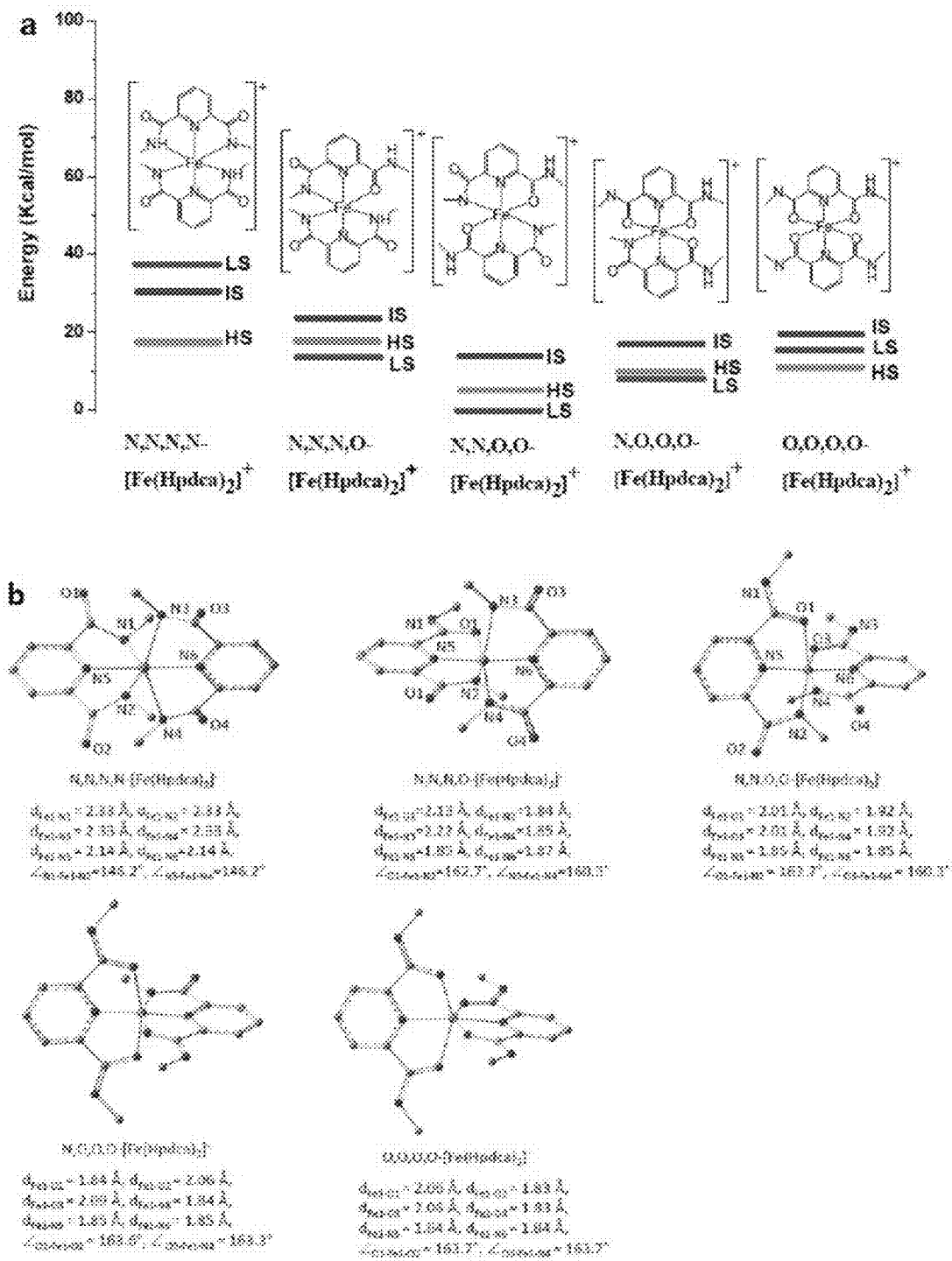
FIG. 11. Density Functional Theory (DFT) calculations. a. The calculated energies of $[Fe(Hpdca)_2]^+$ complexes with different coordination modes and different spin multiplicity, relative to the most stable geometry, which is assigned as 0 Kcal $mol^{-1}$. LS=low-spin (S=1/2); IS=intermediate-spin (S=3/2); HS=high spin (S=5/2); b. Structure and geometrical parameters for the lowest-energy conformation of $[Fe(Hpdca)_2]^-$ in different coordination mode.
Figure 12:
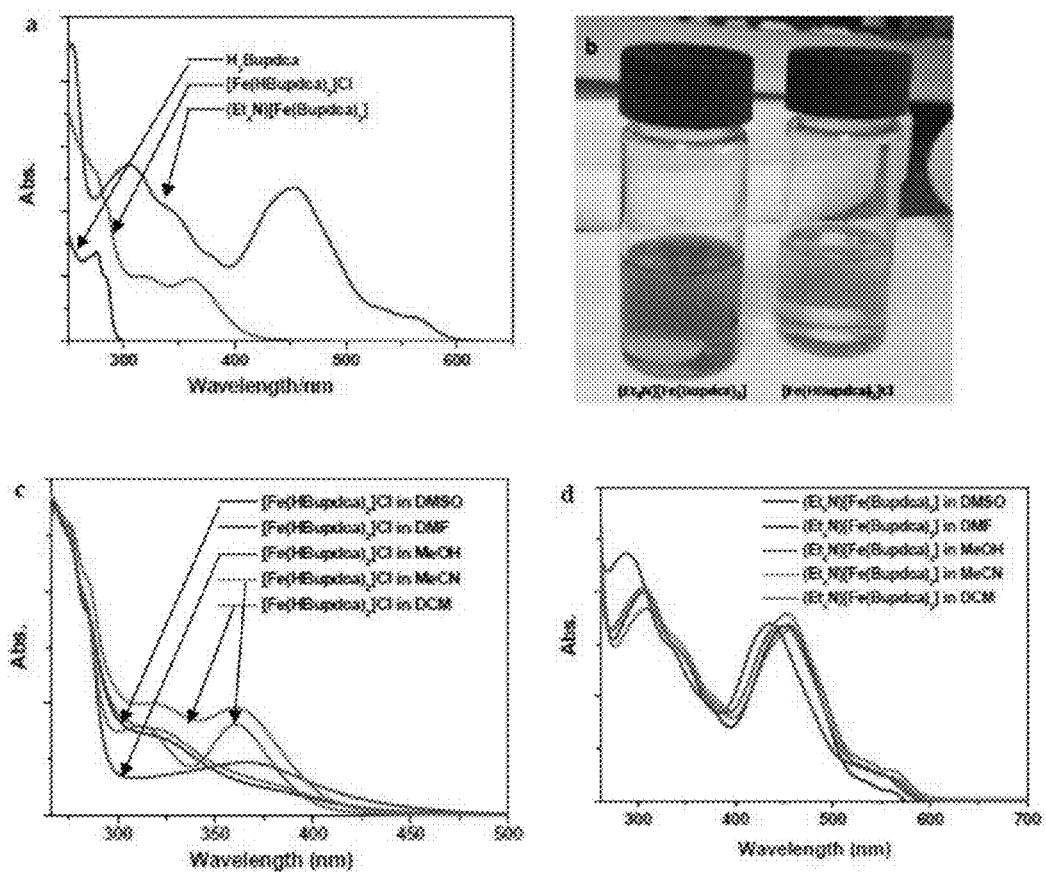
FIG. 12. Absorption spectra. a, UV-Vis spectra of $H_2$Bupdca, $(Et_4N)[Fe(Bupdca)_2]$ and $[Fe(HBupdca)_2]Cl$. The UV-Vis of $[Fe(HBupdca)_2]Cl$ is different from both that of $H_2$Bupdca and $(Et_4N)[Fe(Bupdca)_2]$, indicating that coordination complex was formed after reaction between $H_2$Bupdca and $FeCl_3$, but the resulting complex was not $(Et_4N)[Fe(Bupdca)_2]$. b, Photographs of the of the solutions of $(Et_4N)[Fe(Bupdca)_2]$ and $[Fe(HBupdca)_2]Cl$ in $CH_2Cl_2$. c, Normalized UV-Vis spectra of $[Fe(HBupdca)_2]Cl$ in different solvents, indicating that the complex was decomposed due to the coordination of Fe(III) with the solvent molecules.

In some embodiments, Fe$^{III}$-2,6-pyridinedicarboxamide (pdca) coordination complex is selected for the design. In order to understand the coordination complex formed in polymer networks, a model ligand of 2,6-butylpyridinedicarboxamide (H$_2$Bupdca, Scheme S1) is prepared, and mass spectrometry is used to determine the complex formed using similar conditions as those used for preparing the polymer networks (see Example for details). The measured molecular mass corresponded well with the mass of [Fe(HBupdca)$_2$]Cl as shown in FIG. 10a, indicating in the most stable formed complex just one of the two amide groups was deprotonated upon reacting with FeCl$_3$ without addition of a base. This structure is further characterized and confirmed by UV-Vis and FT-IR spectra as well as DFT calculations (FIGS. 11-13). In comparison, (Et$_4$N)[Fe(Bupdca)$_2$] complex was formed as evidenced from mass spectrometry through the reaction between 2,6-pyridinedicarboxamide and (Et$_4$N)[FeCl$_4$] with addition of NaH as a base (FIG. 10b). (Et$_4$N)[Fe(Bupdca)$_2$] absorbs at a longer wavelength compared to [Fe(HBupdca)$_2$]Cl as shown in FIG. 11. The relative stability of the two complexes is related to the metal-ligand bonding strength. Monitored using UV-Vis spectra (FIG. 11), it is observed that addition of coordinating solvents, such as water, DMF and DMSO, resulted in change in the absorption spectra of [Fe(HBupdca)$_2$]Cl, indicating disassociation of the coordination bond. In contrast, no change was observed for the (Et$_4$N)[Fe(Bupdca)$_2$] complex.

The bonding energy of Fe(III)-N$_{pyridyl}$, Fe(III)-N$_{amido}$, and Fe(III)-O$_{amido}$ bonds are further estimated to be about 145.0, about 82.7 and about 40.7 Kcal/mol, respectively, based on calculation with bond-valence-bond-length correlations (Table 1). The stronger Fe(III)-N$_{pyridyl}$ is comparable to typical covalent bonds, which can be used to enhance the modulus of the material, while the weaker Fe(III)-O$_{amido}$ is almost as weak as hydrogen bonding. As the weak bonding sites are adjacent to the strong bonding sites, they will be stabilized through chelating effect. On the other hand, once the weak bonding sites are broken, the strength of the strong bonding sites will be weakened accordingly, making the coordination structure more fragile. Therefore, the combination of strong and weak bonding sites in a single ligand provides both strong covalent-like crosslinking and energy dissipation mechanisms for strain (FIGS. 1a and 1b).

Figure 1:
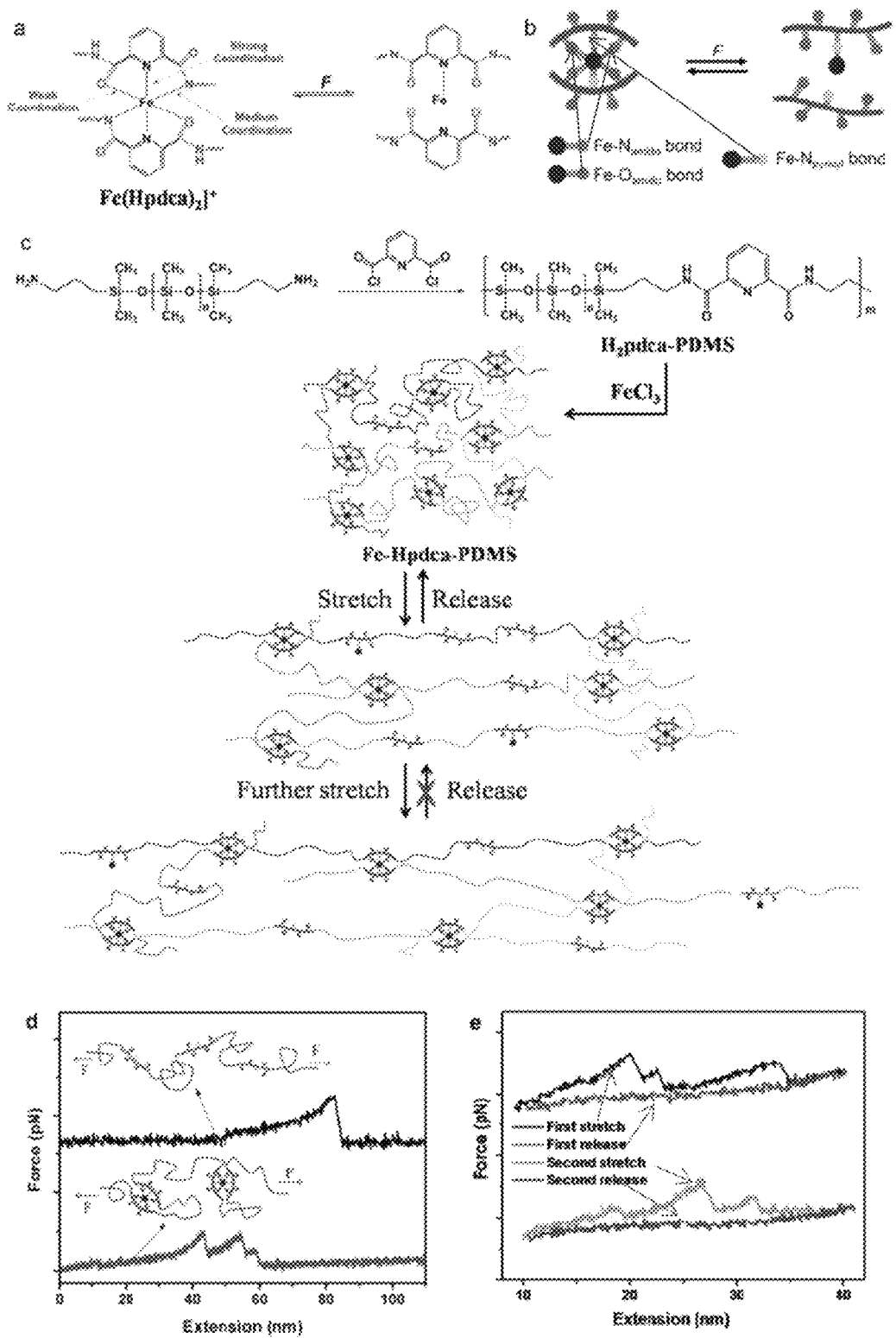
FIG. 1. Schematic structure of material design and results from single-molecule force spectroscopy study. a and b, Schematic illustration of reversible rupture and reconstruction of $[Fe(Hpdca)_2]^+$ complexes during tensile stretching of the films. c, Synthesis and structure of the material and proposed mechanism for chain folding and sliding during tensile stretching. d, Stretching of a single chain of $H_2$pdca-PDMS and Fe-Hpdca-PDMS during force spectroscopy measurement and the resulting typical force-extension curves. e, Typical force-extension curves of the Fe-Hpdca-PDMS from stretching-releasing cycles.

The above metal-ligand design is introduced into a linear poly(dimethylsiloxane) (PDMS) polymer backbone as crosslinking units to allow both good mechanical strength and autonomous healing at room temperature or below (FIG. 1c). Briefly, the PDMS oligomer containing 2,6-pyridinedicarboxamide (H$_2$pdca) groups (denoted as H$_2$pdca-PDMS) were prepared by condensation reactions between bis(3-aminopropyl) terminated poly(dimethylsiloxane) (H$_2$N-PDMS-NH$_2$, Mn=about 5000-7000) and 2,6-pyridinedicarbonyl dichloride to give a colorless viscous liquid. It was subsequently cross-linked by Fe(III) chloride, with a molar ratio of Fe(III) ion to H$_2$pdca ligand of about 1:2, yielding a dark-red solid. The UV-Vis spectrum of the thin film shows a band at about 362 nm, as shown in FIGS. 14 and 15, similar to the absorption wavelength observed for [Fe(HBupdca)$_2$]Cl, indicating the dominant presence of such complexes denoted as Fe-Hpdca-PDMS. Furthermore, the intensity of N—H stretching at about 3315 and about 3335 cm$^{-1}$ partially decreased and a red-shift of the amide C=O stretching frequency was observed in FT-IR spectra (FIG. 16). Raman studies indicate that both Fe—N and Fe—O coordination bonds are present in the as-prepared polymer. The percentage of Fe—O coordination increased with the molar ratio of Fe(III) ion to H$_2$pdca ligand (FIG. 17). In association with the long wavelength tail at λ>about 400 nm in the UV-Vis spectrum, which is more significant in thick films and should be due to the presence of low-energy absorbing Fe(III) complexes (FIG. 15), the resulting polymer network likely contains a mixture of various complexation structures.

Both intra-chain and inter-chain complexations can be present in the Fe-Hpdca-PDMS polymer matrix (FIG. 1c). The intra-chain ones will result in folding of the PDMS chain while the inter-chain ones will give rise to three-dimensional cross-linking. Single-molecule force spectroscopy is used to characterize the presence of the above bonding features. H$_2$pdca-PDMS and Fe-Hpdca-PDMS are first stretched to an extended state. Stretching of H$_2$pdca-PDMS results in just one force peak (FIG. 1d), which corresponds to the detachment of the macromolecule from the substrate. However, stretching of Fe-Hpdca-PDMS leads to sawtooth-like force-extension curves (FIG. 1d), where each individual force peak corresponds to the unfolding of PDMS units through the rupture of the [Fe(Hpdca)$_2$]$^+$ centers. The contour length increments, specified as ΔL$_c$, are 12±2 nm or (12±2)*n nm (n=1-5), corresponds well to one or multiple molecular length of NH$_2$-PDMS-NH$_2$ with Mn of about 5000-7000 (FIG. 18). According to the statistical data of the experiment, the rupture forces of the Fe[(Hpdca)$_2$]$^+$ coordination complexes was about 103 pN (FIG. 19). In order to investigate whether the unfolding and stretching of Fe-Hpdca-PDMS is reversible, the unfolded Fe-Hpdca-PDMS chain is released to zero force. After waiting for about 1 s, the Fe-Hpdca-PDMS chain is stretched again to probe whether it could fold back to its original state. As shown in FIG. 1e, the reversible unfolding-refolding of Fe-Hpdca-PDMS is observed. These features are similar to those in iron-sulfur protein rubredoxin in which single molecule force spectroscopy also reveal characteristic sawtooth features upon single-chain extension. In the case of the polymer of some embodiments, the single chain of Fe-Hpdca-PDMS molecule was elongated upon stretching accompanied by rupture of the [Fe(Hpdca)$_2$]$^+$ coordination complex, while the iron remain bound to one Hpdca-motif, resulting in a meta-stable [Fe(Hpdca)]$^{2+}$ intermediate. The macromolecule can then collapse upon releasing, where the other Hpdca$^-$ can chelate [Fe(Hpdca)]$^{2+}$ to form the [Fe(Hpdca)$_2$]$^+$ center, initiating the complete refolding of Fe-Hpdca-PDMS. Therefore, the single chain Fe-Hpdca-PDMS molecule can be unfolded and refolded due to the rupture and reconstruction of [Fe(Hpdca)$_2$]$^+$ complexes (FIG. 1e and FIG. 20). These dynamic features provide the Hpdca-Fe bonds with dynamic properties, which can break and reform readily at room temperature.

Rheological and Mechanical Properties.

The glass transition temperature (T$_g$) for the resulting polymer network was measured to be below about −90° C. (FIGS. 21 and 22), which is consistent for silicone rubbers. Rheological measurement at room temperature showed that its storage modulus G' is comparable to the loss modulus G" at low frequencies. However, G' increased faster with frequency than G" (FIG. 23a). Such features are characteristic for crosslinked polymer networks and for soft glassy materials. Upon increasing the temperature, both G' and G" decreased but G' decreased more rapidly than G" (FIG. 23b). This indicates that the film becomes more viscous and fluid-like at higher temperature thus potentially facilitating the self-healing. In some embodiments, T$_g$ of a self-healing polymer can be no greater than about 25° C., such as from about −150° C. to about 25° C., from about −150° C. to about −90° C., from about −90° C. to about 25° C., from about −90° C. to about 0° C., or from about 0° C. to about 25° C.

Figure 2:
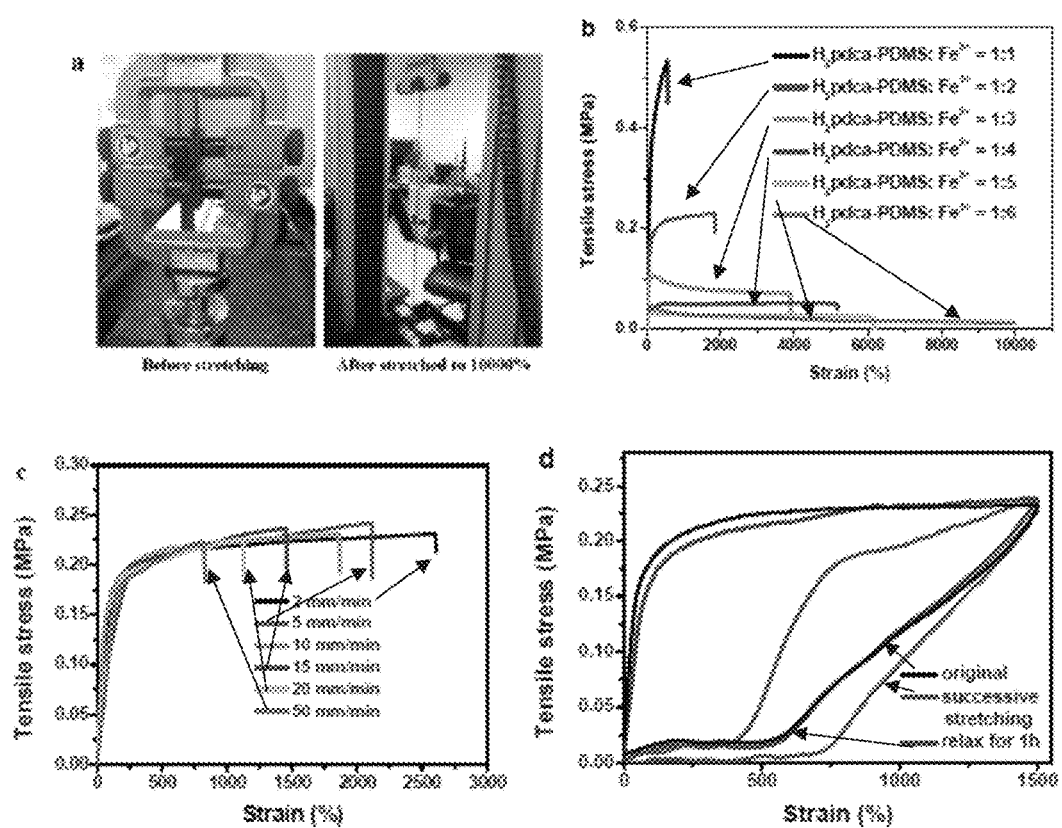
FIG. 2. Mechanical properties of Fe-Hpdac-PDMS polymer. a, Optical image of the film (with the $H_2$pdca-PDMS ligand to Fe(III) metal molar ratio of about 1:6) before and after stretching. b, The tensile stress curves of the film with different molar ratio of $H_2$pdca-PDMS ligand to Fe(III) metal. When the $H_2$pdca-PDMS ligand to Fe(III) metal molar ratio changed from about 1:1 to about 6:1, the modulus decreased while the stretchability increased. Meanwhile, the film became more viscoelastic with the decreasing of Fe(III) ion concentration. As the molar ratio of $H_2$pdca-PDMS ligand to Fe(III) ion changed from about 2:1 to about 1:1, both the nitrogen and oxygen atoms of the amide group will bind to Fe(III) ion, leading to higher crosslinking and poorer chain flexibility. For samples where the ligands are in excess, many uncomplexed ligands are present which increased the probability of collision for coordinating fragments and facilitate bond reformation, leading to higher stretchability. c, The stress-strain curve of the film (with the $H_2$pdca-PDMS ligand to Fe(III) metal molar ratio of about 1:2) with different stretching speeds while keeping the sample width of about 14 mm, thickness of about 1 mm, and gage length of about 2 mm. d, The stress-strain curve of the film (with the $H_2$pdca-PDMS ligand to Fe(III) metal molar ratio of about 1:2) in cyclic stress-strain tests (up to about 1500% strain) in successive stretching and stretching after releasing for 1 h, with a sample width of about 14 mm, thickness of about 1 mm, gage length of about 2 mm and loading rate of about 10 mm $min^{-1}$.

The obtained Fe-Hpdca-PDMS polymer exhibited good mechanical strength and ultra-high stretchability (FIGS. 2a-2d). The Young's modulus of the film is calculated to be 0.54±0.1 MPa from the low strain region (<about 20% strain) of the stress-strain curve (Table 2), indicating the high binding strength of the metal-ligand interaction. The stress-strain curves include an initial stiffening region (where the tension significantly increases with the increase of the strain), followed by a subsequent steady region where the stress is almost constant upon further increase in strain until the film breaks apart. Cyclic stress-strain tests with a maximum applied strain of about 1500% showed pronounced hysteresis, indicating energy dissipation due to bond breakage. There is a pronounced hysteresis in cyclic stress-strain tests even when the sample is subjected to about 30% strain (FIG. 24). However, if the same film was successively stretched and released, the tensional stress of the second stretch was significantly lower than those of the previous cycle. After resting for about 1 hour, the film was observed to almost fully self-recover to its original stress-strain behaviors (FIG. 2d). On the other hand, if the polymer films are stretched and maintained at that strain for about 1 hour, longer time for recovery are involved (partial recovery is observed even after resting for one day). These observations are similar to those for hydrogen-bonding-crosslinked elastomers and hydrogels based on ionic crosslinking, in which the noncovalent bonds break and dissipate the strain energy; after release of the mechanical strain, the broken bonds can be partially recovered to restore most of its mechanical properties.

Surprisingly, Fe-Hpdca-PDMS can be stretched to a much higher strain before fracturing than typical crosslinked PDMS or other supramolecular elastomers (FIGS. 2c and 25). A maximum fracture strain up to about 4500% can be achieved for a sample of about 1 mm in thickness, about 2 mm in gage length, about 6 mm in width at a loading rate of about 2 mm min$^{-1}$ (FIG. 2c). The sample can self-recover to its original length within about one hour after releasing the stress (release immediately after strain). When the amount of metal ions is decreased, at a molar ratio of Fe$^{III}$ to H$_2$pdca at about 1:6, the polymer showed irreversible deformation. With this ratio, the material can be even stretched to over about 100 times its original length without breaking, and can partially recover after resting for about 12 hours (FIGS. 2a, 2b and 26). In comparison, typical covalent-crosslinked PDMS rubbers with similar dimensions exhibit a maximum elongation of 100%-1100%. The best reported hydrogen bonding polymers exhibit reversible stretchability at less than 2000% strain. In some embodiments, a polymer can have stretchability with an elongation (e.g., reversible elongation) of at least about 5×, of an original length or other original dimension, such as at least about 10×, at least about 15×, at least about 20×, at least about 25×, at least about 30×, at least about 35×, at least about 40×, at least about 45×, at least about 50×, and up to about 80×, up to about 90×, up to about 100×, or more, and self-healing can occur at moderate temperatures, such as below, at, or around room temperature or in the range of about −20° C. to about 40° C., about 0° C. to about 40° C., about 10° C. to about 30° C., or about 20° C. to about 30° C. In some embodiments, self-healing can be promoted under mild thermal treatment, such as in the range of about 40° C. to about 80° C., about 40° C. to about 70° C., or about 40° C. to about 60° C.

The ultra-high stretchability can be attributed to the unusual bonding features in the Fe-Hpdca complex. Both intra-chain and inter-chain metal-ligand interactions are present in the Fe-Hpdca-PDMS polymer. The intra-chain metal-ligand interaction results in folding of the PDMS chain allowing large chain extension upon breakage, while the inter-chain metal-ligand interaction leads to the three dimensional cross-linking and potentially repeated bonding/breakage between chains through chain sliding. The dynamic nature of Fe-Hpdca bonds allows it broken and reformed during stretching, leading to unfolding and sliding of the polymer chains, which renders high stretchability of the material. Therefore, this material offers multiple mechanisms for energy dissipation, which makes the material tough (facture energy of about 2571 J/m$^2$, FIG. 27). Additionally, compared with hydrogen bonds, which can dissipate the strain energy just by bond breakage, the Fe-Hpdca complex can offer multiple modes of bond breaking, exchanging and re-formation: i) bond breakage of the weaker carboxamido-Fe$^{III}$ sites while the stronger pyridyl-Fe$^{III}$ bonds hold them in close proximity, and ii) dynamic rupture and reconstruction of the carboxamido-Fe$^{III}$ bonding configurations during chain unfolding and sliding. Unlike the highly directional hydrogen bonds, the Fe-Hpdca bonds are diverging, so that the breakage, reformation and exchange of the bonds can take place more readily.

The proposed carboxamido-Fe$^{III}$ bond reformation/switching mechanism is also supported by experimental observations. Firstly, the stretchability of the films is strongly dependent on stretching speed (FIG. 2c). As the strain-speed increases, less time is allowed for the re-formation of the broken Fe$^{III}$-amide bonds, which reduces the fracture tolerance. Secondly, when different molecular weight PDMS is used (Mn=about 2500-4000 or about 15000-20000) as starting materials, the stretchability of the polymer decreased (FIG. 28). The higher molecular weight PDMS starting polymer has fewer metal-coordination binding sites for bond reconstruction through chain sliding. The lower molecular weight PDMS starting polymer has more metal-coordination binding sites, as evidenced by the increase of stress, but it showed poorer stretchability due to the shorter PDMS chain with reduced folding/unfolding ability.

Self-Healing Properties.

Figure 3:
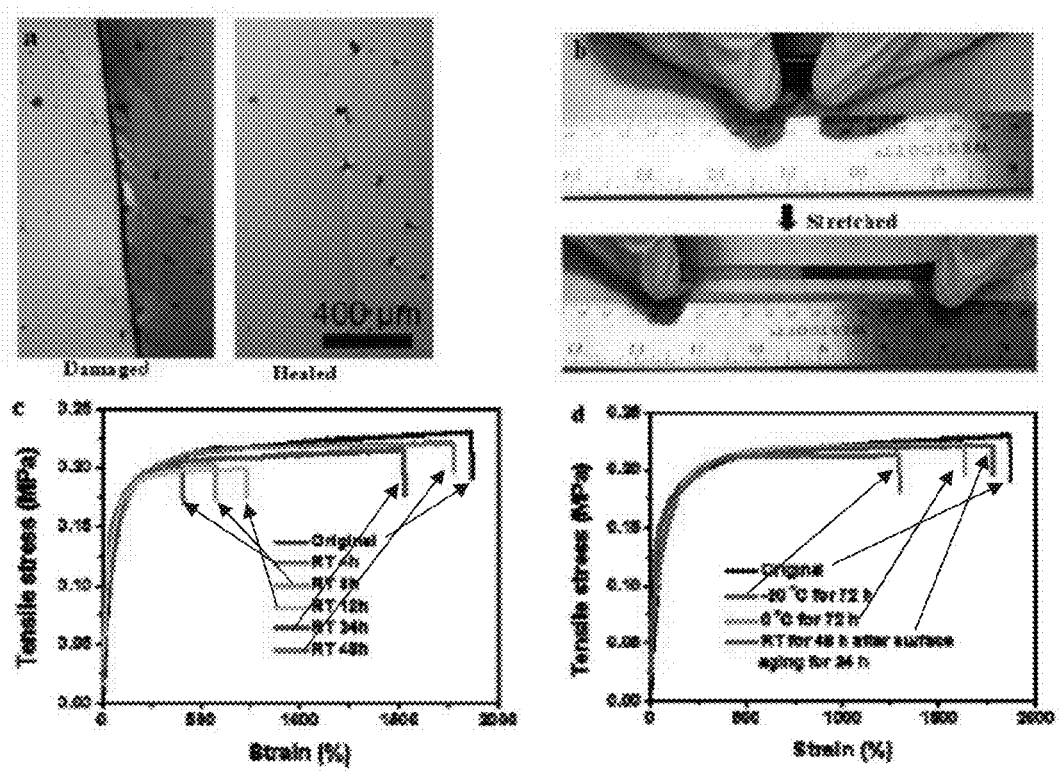
FIG. 3. Self-healing properties of the Fe-Hpdca-PDMS film (with the $H_2$pdca-PDMS ligand to Fe(III) metal molar ratio of about 1:2). a, Optical microscope images of damaged and healed samples. b, Optical images of the healed film before and after stretching. c, The stress-strain curves of the film healed at room temperature (RT) for different times. d, The stress-strain curves of the film healed at about −20° C. and about 0° C. for about 72 h, and the stress-strain curves of the film healed at room temperature for about 48 h after surface aging for about 24 h. Measuring conditions for the tensile test: width of about 14 mm, thickness of about 1 mm, gage length of about 2 mm and loading rate of about 10 mm $min^{-1}$.

The Fe-Hpdca-PDMS polymer has a high stretchability, and also exhibits self-healing capability at or below room temperature. To demonstrate the self-healing capability, the polymer film was cut into two pieces and subsequently put together to allow healing at different conditions (FIGS. 29-31). The cut on the film was observed to almost disappear after healing at room temperature for about 48 h, although minor scars are still visible (FIG. 3a). In order to make the cut region more distinguishable, one of the two pieces was stained using a black dye. As shown in FIG. 3b, the healed film can again sustain a large strain after an about 48 h healing duration at room temperature. A longer healing time and higher healing temperature both resulted in higher recovered fracture strain (FIGS. 3c and 30). The mechanical healing efficiency, $\eta$, is specified as the ratio between the fracture strain restored relative to the original fracture strain. Healing at room temperature for about 48 h led to a recovered fracture strain of about 1700% and a high healing efficiency ($\eta$) of about 90% (FIG. 3c). More generally, $\eta$ can be at least about 10%, at least about 20%, at least about 30%, at least about 40%, at least about 50%, at least about 60%, at least about 70%, at least about 80%, or at least about 90%, and up to about 95%, up to about 98%, up to about 99%, or more. Healing can even take place at about −20° C. and gave a healing efficiency of about 68% after about 72 h (FIG. 3d). This demonstrates autonomous self-healing at a low temperature without the addition of any stimulus.

As a comparison, two undamaged polymer films can also be joined together through self-healing. A film is cut into two pieces and placed in contact with each other through undamaged surfaces (FIG. 32). After healing at room temperature for about 48 h, the rejoined film can sustain about 1060% strain with a healing efficiency of about 47% (FIG. 32b), in contrast to a healing efficiency of about 90% for the cut surface healing under similar conditions (FIG. 3c). The lower healing efficiency is owning to less reactive sites available without cutting and rough surface at the healing site which results in insufficient molecular diffusion. Nevertheless, this indicates the existence of dynamic exchanging of metal-ligand coordination bonds in the polymer matrix.

Unlike self-healing materials based on hydrogen bonding, the self-healing of the film is less sensitive to surface aging. Upon cutting the film into two separate pieces, left apart in ambient temperature for about 24 h, and then healed at room temperature for about 48 h, it is observed that the healing efficiency still reached about 90%, a value similar to the healing efficiency of freshly cut and healed pieces (FIG. 3d). The cycle of stretching, breaking and healing can be repeated multiple times. The excellent self-healing properties of Fe-Hpdca-PDMS are attributed to two factors: (i) the presence of abundant dynamic metal-ligand coordination bonds; and (ii) the low $T_g$ (below about −90° C.) of the polymer affords high mobility of the polymer chains to afford self-healing, even at low temperature.

Application in Artificial Muscles.

Dielectric elastomers are electroactive polymers that are particularly attractive for artificial muscles. To achieve highperformance actuators, the properties of the elastomer should include high stretchability, a large dielectric constant and, more importantly, a large dielectric strength. Dielectric elastomer actuators have been equipped with self-healing mechanisms based on the use of (i) liquid dielectrics, which redistribute after dielectric breakdown, and thus restore the insulating properties of the dielectric film, and (ii) self-clearing nanotube electrodes, which prevent electrical shorting after dielectric breakdown events.

In addition to the excellent stretchability and low temperature self-healing, Fe-Hpdca-PDMS film with the H$_2$pdca-PDMS ligand to Fe(III) metal molar ratio of about 1:2 has a high dielectric constant (about 6.4) (FIG. 33) and a high dielectric strength (un-optimized result gives: about 18.8 MV/m), at comparable magnitude to commercial rubbers measured under similar conditions (at an unstretched state with soft electrodes of large area). These properties make Fe-Hpdca-PDMS a desirable candidate as an artificial muscle. More generally, a self-healing polymer can have a dielectric constant of at least about 2.5, at least about 3, at least about 3.5, at least about 4, at least about 4.5, at least about 5, at least about 5.5, or at least about 6, and up to about 6.5, up to about 7, up to about 7.5, or more, and can have a dielectric strength of at least about 1 MV/m, at least about 2 MV/m, at least about 3 MV/m, at least about 4 MV/m, at least about 5 MV/m, at least about 6 MV/m, at least about 7 MV/m, at least about 8 MV/m, at least about 9 MV/m, at least about 10 MV/m, at least about 13 MV/m, at least about 15 MV/m, at least about 17 MV/m, or at least about 18 MV/m, and up to about 19 MV/m, up to about 20 MV/m, or more.

Figure 4:
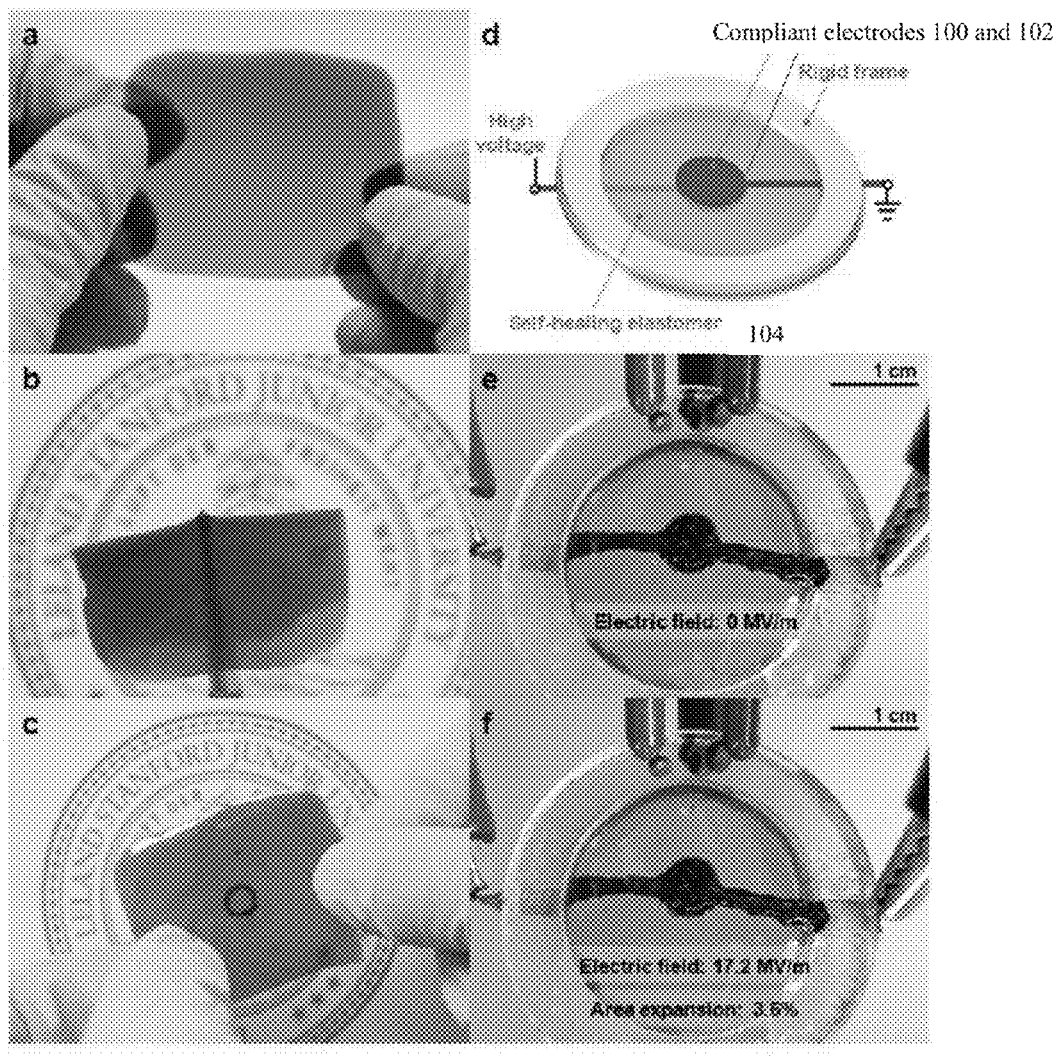
FIG. 4. Self-healing artificial muscle fabricated from Fe-Hpdca-PDMS film with the $H_2$pdca-PDMS ligand to Fe(III) metal molar ratio of about 1:2. a, Pristine film of the self-healing elastomer. b, A pointed object penetrated the film and caused severe mechanical damage. c, Condition of the sample after about 72 h of healing at room temperature. The location of former mechanical damage was marked with a circle. d, Experimental setup to assess the aptitude of the healed sample for use in a dielectric elastomer actuator. Two circular, rigid frames held the elastomeric film 104 in place. The location of former mechanical damage was sandwiched between compliant electrodes 100 and 102, which applied a high electric field from a voltage source across the thickness of the elastomer and caused the area sandwiched by electrodes 100 and 102 to expand. e and f, Photos of the dielectric elastomer actuator before and after the application of high voltage. The high electric field induced an area expansion of about 3.6%, but it did not cause dielectric breakdown at the location of the self-healing event.

Here, a self-healing artificial muscle is fabricated, where the self-healing property of the dielectric elastomer film is directly utilized. FIG. 4 shows a pristine elastomer film of Fe-Hpdca-PDMS with a thickness of about 640 being punctured by a sharp pointed object (FIG. 4b). The sample was subsequently stored for about 72 h at room temperature. A square-wave high-voltage signal (about 1 Hz; about 11 kV maximum voltage; 0 kV minimum voltage) was then applied through coated carbon electrodes over the healed region, causing the dielectric elastomer actuator to visibly deform. FIGS. 4e and f show still-images of the actuator at 0 kV (0 MV/m) and about 11 kV (>about 17.2 MV/m), respectively. The high applied electric field caused an area expansion of about 3.6% in the elastomer; however, it did not cause any electric breakdown at the location of mechanical damage. The ability to withstand electric fields above about 17 MV/m after self-healing indicates the excellent self-healing ability of the material. By increasing the maximum voltage of the square wave signal to about 12 kV (>about 18.8 MV/m), the electric breakdown of the sample is observed. Despite the inflicted damage, the self-healed film still retained values comparable to the pristine polymer. The developed Fe-Hpdca-PDMS elastomer is highly tunable and can be further optimized for specifications of an actuator.

In summary, some embodiments are directed to a highly stretchable and autonomous self-healing material by incorporating ligands with various bond strengths. This material is capable of sustaining a large strain, in which the strong bonding sites hold the weaker bonding ligands in close proximity with the metal ion allowing a dynamic bond-breakage and reformation process induced by strain. The incorporation of the above ligands into a linear PDMS polymer backbone as repeating units allowed additional mechanism for energy dissipation during stretching through metal-ligand interaction by intra-chain folding and inter-chain sliding mechanisms. The as-prepared material can be stretched to about 45 times of its original length and recovered upon releasing. The film displayed excellent self-healing properties even at low temperature down to about −20° C., in the absence of any healants, plasticizers, solvents, or external energy. Its suitability for artificial muscle applications is demonstrated by leveraging the material's ability to restore a high dielectric strength after recovery from mechanical damage.

Figure 5:
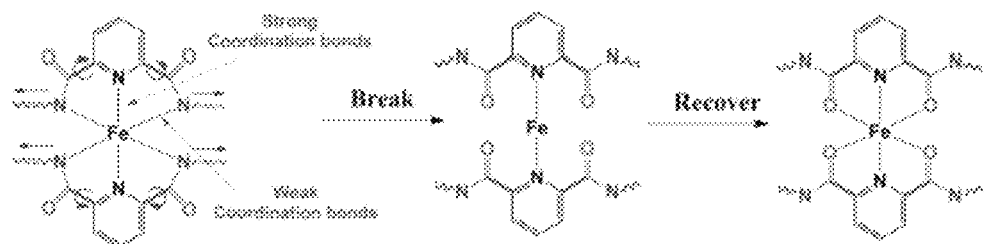
FIG. 5. Proposed ligand design. The ligand combines both strong (pyridinyl-metal) and weak (amido-metal) bonding sites. The strong bonding sites enhance the mechanical property while the weak bonding sites allow self-healing. The ligand design allows strain-induced simultaneous bond breakage and re-formation in Fe(III) complexes.

In some embodiments, the approach to develop dynamic metal-ligand coordination is to combine multiple bonding strengths into a single ligand, such as a poly-dentate ligand (FIG. 5). It is also contemplated that multiple bonding strengths can be included in different ligands. Three categories can be identified according to bond strength: i) strong binding sites: metal ions with nitrogen atoms on pyridyl or pyridinyl groups (M-pyridinyl) and with carboxylic acid groups (M-COOH). The use of such binding sites can enhance the mechanical strength of the resulting material; ii) medium-strength binding sites: metal ion interaction with nitrogen atoms on amide groups (M-N$_{amido}$). These bonds provide partial mechanical strength enhancement while allowing self-healing at or close to room temperature; and iii) weak binding sites: metal ion interaction with oxygen atoms on amide groups (M-O$_{amido}$). Such bonding sites are used for room temperature self-healing. It is noted that depending on the metal ion used, the bond strength may be stronger for M-O$_{amido}$ than for M-N$_{amido}$. By designing ligand moieties or structures comprising all three binding sites at different ratios and geometries, a range of metal-ligand coordination cross-linkers can be obtained with both good bond strength and dynamic features. The ligands combined with different metal ions can provide a class of self-healing polymers with the capability of fine-tuning of various bond strengths. The mechanical properties of the polymers can be further controlled by incorporation of additional cross-linking mechanisms. More generally, a single type of ligand or multiple types of ligands can include multiple bonding (or metal coordination) sites, such as a first bonding site having a first bonding strength (e.g., nitrogen atoms in monocyclic and polycyclic heteroaryl groups, carboxylic acid groups, and other carbonyl-containing groups), a second bonding site having a second bonding strength (e.g., nitrogen atoms in amide, amine, and urea groups), and a third bonding site having a third bonding strength (e.g., oxygen atoms in amide groups), where the first bonding strength>second bonding strength>third bonding strength.

Apart from the ligand structures, the types of metal ions can be adjusted to tune properties of the metal-ligand interactions. Different metal ions can have different coordination numbers, bond lengths, and bonding strength. The combinations of the metal ions and the different ligands can provide a variety of metal-ligand motifs, and lead to self-healing materials with controllable healing speed, healing efficiency, and mechanical strength. Metal ions can be selected from, for example, transition metal ions (e.g., from Groups 3, 4, 5, 6, 7, 8, 9, 10, 11, and 12 of the Periodic Table) and metal ions of lanthanides. Valence of a metal ion can be 1+, 2+, 3+, 4+, or higher.

The pyridinedicarboxamide (pdca) ligand can chelate to various metal ions. Changing these ions can vary the impact of various bond strengths on self-healing and mechanical properties of the resulting polymers. Different metal ions like $Zn^{2+}$, $Fe^{2+}$, $Fe^{3+}$, $Co^{3+}$, $Eu^{3+}$, and so forth can have different coordination numbers and various binding strength. For example, ions like $Zn^{2+}$ and $Eu^{3+}$ can bind much stronger with O$_{amido}$ sites, while $Co^{3+}$ can bind stronger with $N_{amido}$. In some embodiments, metal ions with a stronger bonding strength through either N or O may not be as stretchable as the Fe(III) complex, as bond-reformation during strain may be reduced due to the broken bonds rotating into unfavorable conformation due to strain.

Some embodiments of self-healing polymers incorporate pdca ligands, such as linear PDMS polymers with pdca ligands incorporated into the PDMS backbone. The pdca sites serve as cross-linking sites upon addition of metal ions due to the bi-dentate and tri-dentate complexation of metal-ligands. PDMS with various molecular weights can be used for the synthesis of PDMS-pdca polymers. In place of, or in addition to PDMS, other polysiloxane chains can be used, as well as polyamide chains, polyisobutene chains, polyolefin chains, polyester chains, and polyurethane chains, for example.

Figure 6:
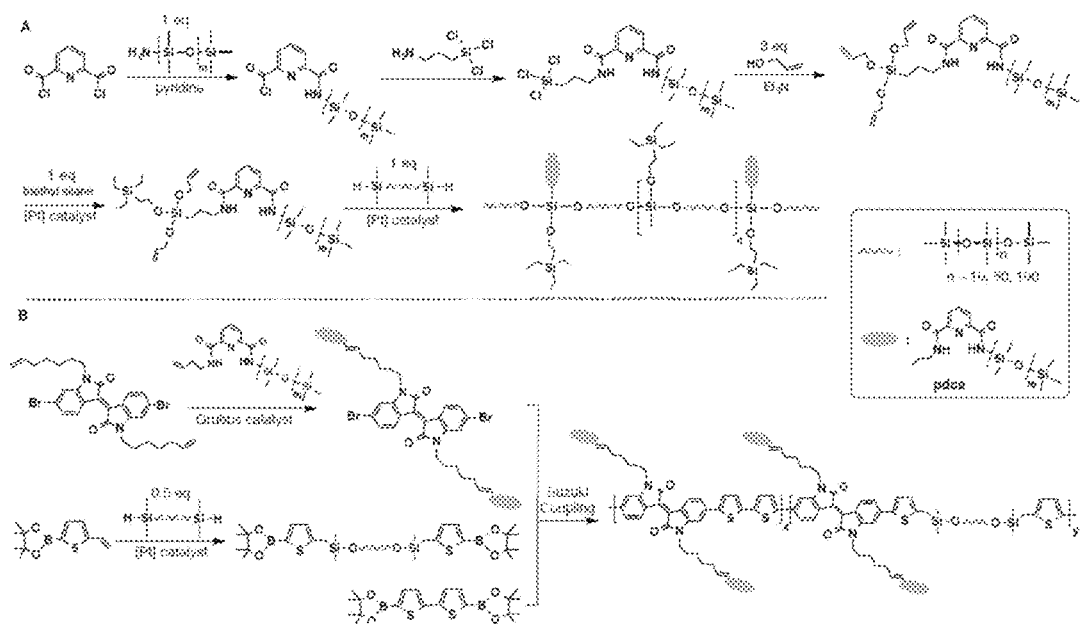
FIG. 6. Examples of polymers with pdca ligands as sidechains. (A) Flexible PDMS-type polymers as the polymer backbone. (B) Rigid conjugated polymer backbone. A small fraction of monomers with flexible spacers can be introduced into the polymer backbone to lower $T_g$ of the resulting polymer.

In other embodiments, the polymer architecture can be varied to tune the self-healing and mechanical properties of the resulting materials. For example, pdca moieties can be incorporated as side groups (FIG. 6A). When the main chain PDMS-pdca polymer is under strain, the chain disentanglement may directly place stress on the metal-ligand units and induce dynamic bond switching around a Fe(III) center. In contrast, with the pdca moieties on the side chains, the strain energy may be first dissipated through the main chain disentanglement, followed by unzipping of the pdca-Fe units. The spacer length and flexibility also may affect the onset strain for pdca-metal bond breakage.

In addition to flexible PDMS backbones, the polymer backbone rigidity can be tuned by replacing PDMS with more rigid conjugated backbones or with conjugated portions separated by flexible linkages (FIG. 6B). For example, iso-indigo-containing polymers can be used. The tendency for π-π stacking between the conjugated units can also serve as a mechanism for improving the mechanical strength of the resulting polymers. The $T_g$ of these polymers, however, may be higher than the PDMS polymers. Therefore, heating may be involved for self-healing.

Figure 7:
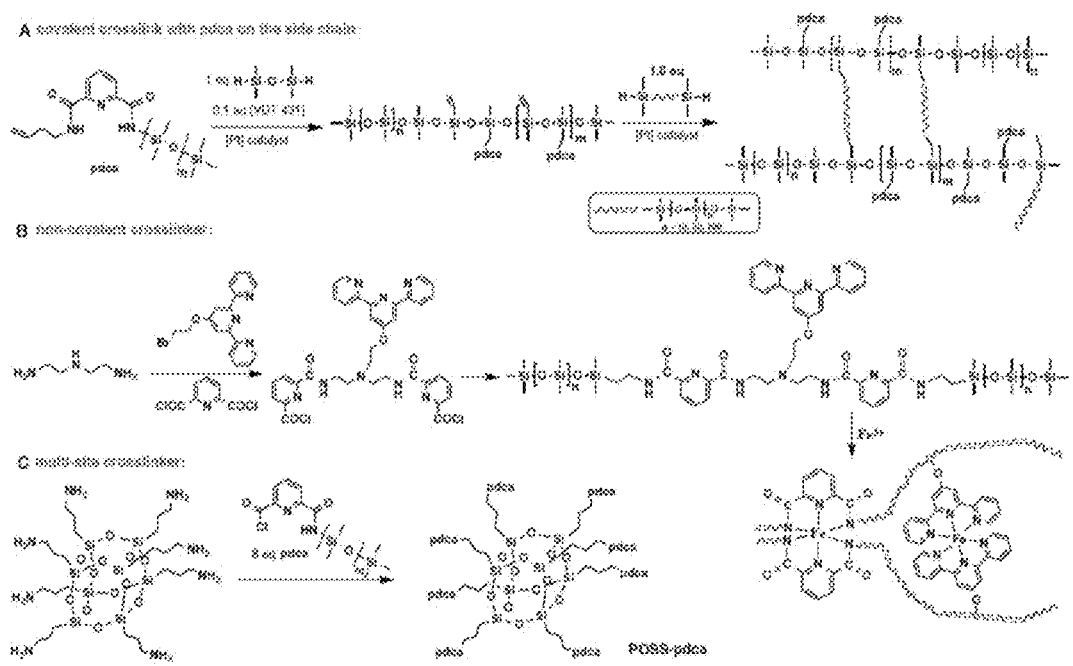
FIG. 7. Examples of self-healing polymers with enhanced mechanical properties through cross-linking. (A) Covalent cross-linking; (B) Non-covalent cross-linking; (C) Multi-site cross-linker.

Addition of covalent cross-linking is another strategy to increase the mechanical strength of polymers, such as flexible PDMS units, aliphatic, aryl C—C bond, and strong metal-ligand coordination bonds (FIG. 7A). The rotational barriers and bond strengths of these cross-linkers can be quite different, allowing systematically tuning of the mechanical and self-healing properties of pdca-PDMS polymers. Non-covalent cross-linking also can be incorporated (FIG. 7B).

Another example to induce additional cross-linking takes advantage of multi-functionalized polyhedral oligomeric silesesquioxanes (POSS) (FIG. 7C). POSS can be considered small silica particles with a nano-sized cage structure. With multi-functional groups on its cage vertices, POSS can enhance the mechanical strength of the resulting polymers with a small amount being added. This can allow the resulting polymer to maintain a high density of self-healing bonds and facilitates both fast healing and high mechanical strength. POSS can be synthesized with multiple pdca ligands (FIG. 7C), and further blended into the pdca-PDMS polymer matrix. The multi-pdca functionalized POSS can serve as a nano-sized cross-linker to coordinate with pdca-PDMS chains via Fe with a high cross-linking density.

Figure 8:
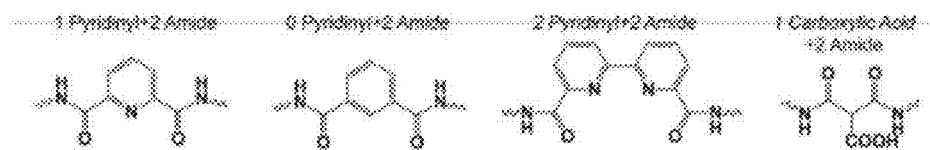
FIG. 8. Example structures for metal-ligand coordination.

Also, different ligands can be used to tune molecular structures of the ligands and change the ratios between strong coordination sites and weak coordination sites. FIG. 8 illustrates some examples of ligand structures. In these ligand structures, various amounts of M-Pyridinyl, M-$N_a$-$_{mido}$, and M-$O_{amido}$ bonds are included to provide a variety of strong and weak bonding interactions.

Stretchable and self-healing polymers also can be based on other metal-ligand systems, such as dynamic coordination within tris(pyrid-2-yl)amine with $Zn^{2+}$ ions and 2,2'-bispyridine with metal ions.

Figure 9:
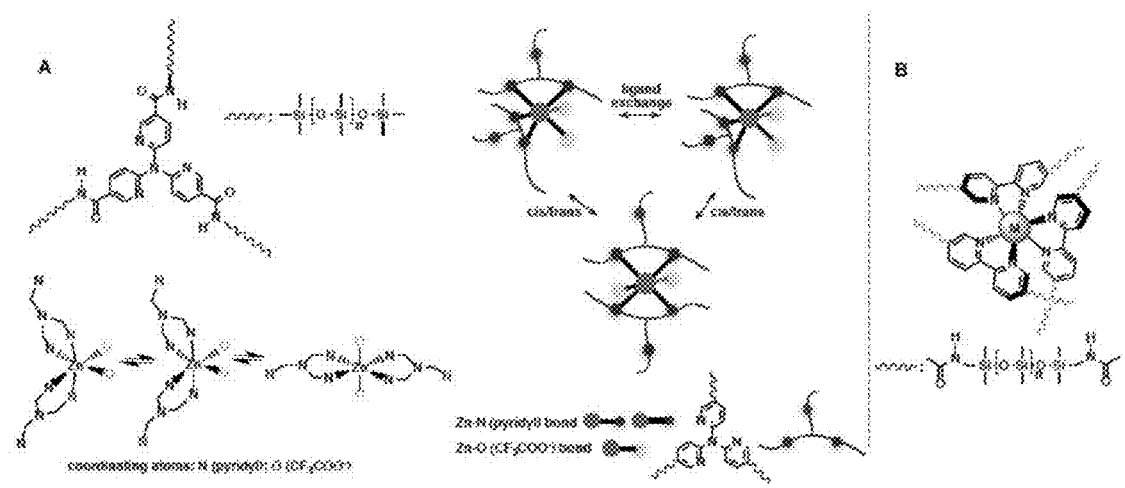
FIG. 9. Other example structures. (A) Tris(pyrid-2-yl) amine moiety can have a variety of possible bonding configurations with $Zn^{2+}$ ions. This can result in strain-induced simultaneous bond breakage and re-formation. (B) Incorporation of stronger bonding bpy-M as potentially strong crosslinking sites. The ability of $Zn^{2+}$ ions to inter-convert between tetrahedral and octahedral coordination geometry with bpy ligands can act as another system that can undergo strain-induced bond reformation, endowing high stretchability.

For example, tris(pyrid-2-yl)amine moiety can be chosen to take advantage of its propeller-shaped geometry of the three pyridinyl rings and its dynamic coordination bonding to $Zn^{2+}$ ions. With trifluoroacetate counter anions, bidentate tris(pyrid-2-yl) $Zn^{2+}$ complexes can be highly fluxional in solution, with the coexistence of both cis-trans isomerization and exchange of the third non-coordinating pyridinyl nitrogen donor (FIG. 9A). The dynamic bonding within the $Zn^{2+}$ ions and tris(pyrid-2-yl)amine moieties can serve a mechanism for energy dissipation. This system may also exhibit strain-induced simultaneous bond breakage and reformation, thus providing the materials with high stretchability and self-healing ability. In addition, since the free ligand and $Zn^{2+}$ salt are not luminescent, the bright blue luminescence of these octahedral $Zn^{2+}$ complexes can allow monitoring the dynamic switching effect during stretching via luminescence change.

2,2'-bipyridine (bpy) is a versatile bidentate ligand for a variety of metal ions, such as $Fe^{2+}$, $Zn^{2+}$, $Co^{2+}$, and $Ru^{2+}$. These metal ions typically adopt an octahedral geometry and bind to the 2,2-bipyridine ligands in an about 1:3 ratio. Such 2,2'-bipyridine can be co-polymerized at various ratios with PDMS and pdca using the amine-acyl chloride chemistry. The metal-bpy complexation will associate with three chains to form crosslinks (FIG. 9B). Additionally, they offer stronger bonding than the pdca-metal bonding, allowing multiple bonding strengths and mechanisms for energy dissipation. Kinetically stable $Ru(bpy)_3^{2+}$ chelation can allow the formation of a tough polymer framework while $Zn^2$ can give both tetrahedral and octahedral complexes with di-imine ligands. The ability of $Zn^{2+}$ ions to interconvert between tetrahedral and octahedral coordination geometry can act as another system that can undergo strain-induced bond reformation, endowing the property of high stretchability.

Example

The following example describes specific aspects of some embodiments of this disclosure to illustrate and provide a description for those of ordinary skill in the art. The example should not be construed as limiting this disclosure, as the example merely provides specific methodology useful in understanding and practicing some embodiments of this disclosure.

Methods

Materials and Measurements.

Bis(3-aminopropyl) terminated poly(dimethylsiloxane) ($H_2$N-PDMS-$NH_2$, Mn=about 2500-4000, about 5000-7000, about 15000-20000, respectively) were purchased from Gelest. The remaining chemicals and solvents were purchased from Sigma-Aldrich. All of the chemicals were used as received without further purification. NMR ($^1$H and $^{13}$C) spectra were recorded on a Varian Mercury 400 NMR spectrometer in deuterated solvents at room temperature. Infrared spectra were recorded with a Horiba Jobin-Yvon Fluorolog-3 fluorometer. Absorption spectra were recorded on an Agilent Cary 6000i UV/Vis/NIR Spectrophotometer. Analytical gel permeation chromatography (GPC) experiments were performed on a Malvern VE2001 GPC solvent/sample Module with three ViscoGEL™ I-MBHMW-3078 columns. The calibration was based on polystyrene standards with narrow molecular weight distribution. Differential Scanning calorimetry (DSC) experiments were performed using a Model Q2000 from TA Instruments. The temperature range was about −90 to about 100° C., at a heating and cooling speed of about 10° C./min. Dynamic mechanical analysis measurement was carried out on dynamic mechanical Analyzer TA Instrument Q800 (strain rate of about 0.01 mm/mm; frequency sweeps at about 0.1-10 Hz; Temperature: about −90 to about 10° C.). The rheological characterizations were carried out on a HAAKE RheoStress 6000 rheometer. Frequency and temperature sweeps were performed with about 2 mm parallel plates on circular samples with about 2 mm diameter. Frequency sweeps at about 0.1-100 Hz were measured at about 0.1% strain at room temperature (20° C.). Temperature sweeps were run from about 20° C. to about 80° C. at about 1 Hz, with the strain automatically modulated at 0.3%+/−0.2% by the instrument to keep the measured torque at a reasonable value as the sample softened. Contact with the sample was maintained by the auto-compression feature set to 0.2+/−0.15 N.

Synthesis of $H_2$pdca-PDMS Ligand.

$Et_3N$ (about 3.5 mL) was added to a solution of $H_2N$-PDMS-$NH_2$ (about 50 g, Mn=about 5000-7000) in anhydrous $CH_2Cl_2$ (about 80 mL) at 0° C. under argon atmosphere. After stirring for about 2 hours, a solution of 2,6-pyridinedicarbonyl dichloride (about 2.04 g, about 10 mmol) in $CH_2Cl_2$ (about 20 mL) was added dropwise. The resulting mixture was stirred for about 2 hours while the temperature was kept at 0° C. with ice water. The solution was then allowed to warm to room temperature and stirred for about 2 days. After reaction, the solution was concentrated to about ¼ of its volume and about 60 mL MeOH was poured into it to quench the reaction. White precipitate-like viscous liquid appeared and the mixture was settled for about half an hour. The upper clear solution was then decanted. About 20 mL $CH_2Cl_2$ was added to dissolve the product. The dissolution-precipitation-decantation process was repeated for three times and the final product was subjected to vacuum evaporation to remove the solvent and trace of $Et_3N$. Yield: about 35 g (about 75%). Molecular weight according to GPC: about 107,670 (PDI=about 1.3) (FIG. 34). $^1H$ NMR (400 MHz, $CDCl_3$): δ about 8.36 (d, J=8.0 Hz, 2H), about 8.02 (t, J=8.0 Hz, 1H), about 7.77 (s, 2H). $^{13}C$ NMR (400 MHz, $CDCl_3$): δ about 163.68, about 149.18, about 139.11, about 125.16 (FIG. 35).

Two other $H_2$pdca-PDMS polymers with different percentage of $H_2$pdca moiety were prepared by using $H_2N$-PDMS-$NH_2$ with Mn of about 2,500-4,000 (the product is denoted as $H_2$pdca-PDMS') and about 15,000-20,000 (the product is denoted as $H_2$pdca-PDMS"), respectively, as the starting materials. Molecular weight according to GPC: about 52,614 (PDI=about 1.6) for $H_2$pdca-PDMS' and about 119,700 (PDI=about 1.4) for $H_2$pdca-PDMS". $^1H$ NMR and $^{13}C$ NMR are similar to $H_2$pdca-PDMS (FIGS. 36-37).

Preparation of Fe-Hpdca-PDMS Films.

Typical procedure for the preparation of Fe-Hpdca-PDMS films is: a certain amount of $FeCl_3$ (about 100 mg/mL) solution in methanol (determined by the molar ratio of $H_2$pdca ligand to Fe(III)) was added to a solution of $H_2$pdca-PDMS (about 1 g) in $CH_2Cl_2$ (about 5 mL). Base such as NaH was not used in order to avoid the NaCl impurity since Fe(III) can promote the deprotonation of amide groups before complexation. The mixed solution was stirred for about 1 day at room temperature and then concentrated to about 2 mL. The concentrated solution was poured into a polytetrafluoroethene (PTFE) mold measuring about 36 mm length×about 14 mm width×about 3.0 mm height and dried at room temperature for about one day followed by drying at about 100° C. for about 12 h. The as-prepared film has a size of about 36 mm length×about 14 mm width×about 1.0 mm height. The films were then peeled off from the PTFE mold for further testing.

Single-Molecule Force Spectroscopy Study.

Single molecule force experiments on $H_2$pdca-PDMS and Fe-Hpdca-PDMS macromolecules were performed on a modified AFM. Each $Si_3N_4$ AFM cantilever (MLCT, Bruker, Santa Barbara, Calif.) was calibrated in solution before each experiment, showing a spring constant of about 130 pN $nm^{-1}$. All experiments were performed in toluene at room temperature. For the experiment of $H_2$pdca-PDMS, a toluene solution (about 150 mg/mL) was used. For the experiment of Fe-Hpdca-PDMS, the toluene solution (about 150 mg/mL) of $H_2$pdca-PDMS was diluted to a final concentration of about 15 mg/mL with MeOH/Toluene (v/v=about 1/10) solution of $FeCl_3$ (about 5 mg/mL). In a typical experiment, the solution was deposited on a clean glass coverslip and allowed to dry. One drop of toluene was added before stretching. The macromolecules were then stretched under a constant pulling speed of about 1000 nm/s. In order to investigate whether the unfolding and stretching of Fe-Hpdca-PDMS is reversible, the unfolded Fe-Hpdca-PDMS chain is released quickly to zero force. After waiting for about 1 s, the Fe-Hpdca-PDMS is stretched again to probe whether it could fold back to its original state.

Mechanical and Self-Healing Tests.

Mechanical tensile-stress experiments were performed using an Instron 5565 instrument. Three samples were tested for each polymer composition. Tensile experiments were performed at room temperature at different sample size and strain rate when evaluating the stretchability. For cyclic stress-strain test, mechanical tests for ligand-density-dependence and self-healing experiments, sample size was about 75 mm length×about 14 mm width×about 1.0 mm height with a strain rate of about 10 mm $min^{-1}$. For self-healing tests, the film was cut into two pieces and then put together. The film was then healed at different temperatures for different durations. The healed films were then stretched following the same procedure to obtain the stress-strain curves.

Preparation of Dielectric Elastomer Films.

About 1 g of $H_2$pdca polymer was dissolved in about 5 mL of dichloromethane, which was mixed with about 0.25 mL of methanol solution of $FeCl_3$ (about 100 mg/mL). The mixture was stirred overnight and then concentrated to about 1-2 mL into a viscous red liquid. The liquid was poured onto fluorinated glass, dried in air at room temperature for about 2 h and about 80° C. for about 12 h. The polymer film was then peeled off from the fluorinated glass.

Measurement of Dielectric Constant.

To fabricate the capacitors for dielectric constant measurements, an about 350 μm Fe-Hpdca-PDMS film was firstly heat pressed onto P-doped Si wafer. EGaIn was used as the top electrode. The capacitance data were collected using an LCR meter (Agilent E498E precision LCR meter) controlled with a LabView Script. The dielectric constant was calculated from the capacitance.

Preparation of Actuators.

Two circular, rigid rings (fabricated from acrylic plates; inner diameter of rings: about 30 mm) held the elastomer film in a flat position. The location of former mechanical damage (marked with a circle) was coated with circular, compliant electrodes (carbon conductive grease; MG Chemicals) on both sides. Thin lines of carbon grease connected the circular electrodes with the external electrical circuit.

Determination of Coordination Configuration Using Model Ligands

In order to determine the specific coordination configuration of the Fe(III)-2,6-pyridinedicarboxamide complex, a model ligand (2,6-butylpyridinedicarboxamide, $H_2$Bupdca, Scheme S1) is prepared and its complexation with Fe(III) is evaluated.

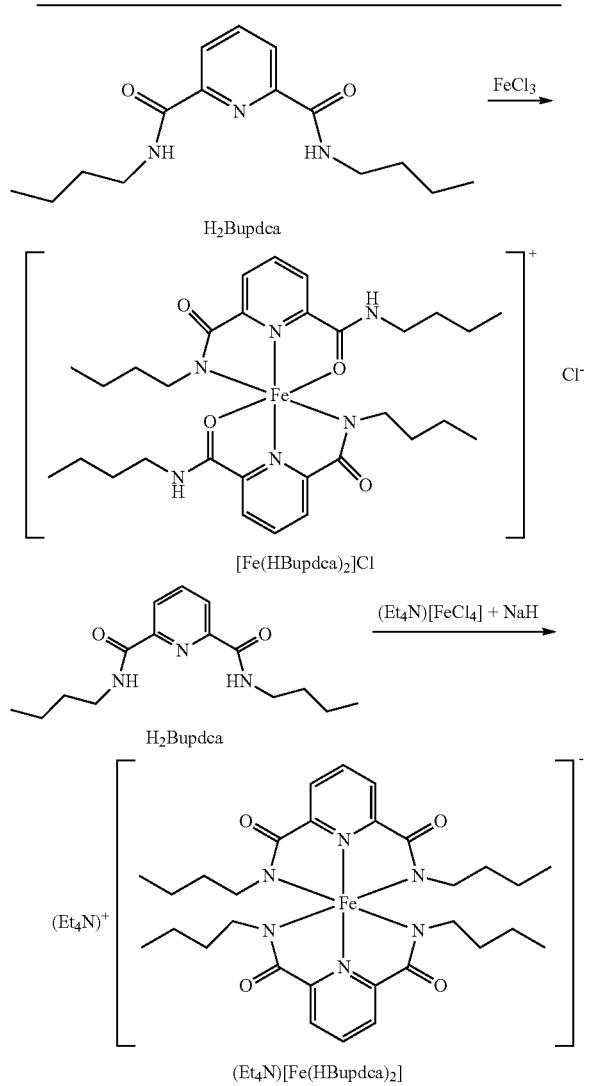

Scheme S1 | The molecular structure of model ligand $H_2$Bupdca and Fe(III) complexes derived from different procedures $H_2$Bupdca was synthesized according to typical procedures with modifications: 2,6-Pyridinedicarboxylic acid chloride (about 502 mg, about 2.46 mmol) and N-butylamine (about 359 mg, about 4.90 mmol) were reacted under argon for about 3 h at room temperature in presence of excess pyridine (about 4.1 g, about 51.90 mmol) and using diethyl ether (about 50 ml) as a solvent. The resulting pyridinium hydrochloride precipitate was removed by filtration, and the solvent in the filtrate was removed by rotary evaporation. The resulting solid was collected and dissolved in dichloromethane, washed with aqueous about 5% $NaHCO_3$, and dried over $Na_2SO_4$. Evaporation of the solvent gave the ligand $H_2$Bupdca with a good yield (about 95%). $^1$H NMR ($CDCl_3$, 400 MHz) δ (ppm) about 8.34 (d, J=7.5 Hz, 2H), about 8.04 (t, J=7.5 Hz, 1H), about 7.75 (b s, 2H, NH), about 3.50 (t, J=6.0 Hz, 4H), about 1.65 (quint, J=6.0 Hz, 4H), about 1.42 (m, 4H), about 1.01 (t, J=6.0 Hz, 6H). MS (ESI) m/e=about 277.76 ($M^+$). Selected FT-IR absorption bands (KBr pellet, $\nu/cm^{-1}$): about 3278 ν(N—H); about 1649 ν(amide I); about 1531 ν(amide II). Analysis for $C_{15}H_{23}N_3O_2$: found, C about 64.98, H about 8.40, N about 15.18; calculated C about 64.95, H about 8.36, N about 15.15.

Two procedures were used to study the coordination behavior of the $H_2$Bupdca ligand with Fe(III). First, typical procedures were to prepare the Fe(III)-2,6-pyridinedicarboxamide complexes ($Et_4N$)[Fe(Bupdca)$_2$] by using NaH as a base. The ligand $H_2$Bupdca (about 139 mg, about 0.50 mmol) was dissolved in anhydrous N,N'-dimethylformamide (DMF) (about 5 mL) and followed by addition of solid NaH (about 40 mg, about 1.66 mmol) under argon atmosphere. The solution was stirred for about 1 h. ($Et_4N$)[$FeCl_4$] (about 82 mg, about 0.25 mmol, synthesized by mixing anhydrous $FeCl_3$ and $Et_4NCl$ in methanol) was dissolved in anhydrous DMF (about 5 mL) and added dropwise to the previous solution. The resulting red solution was stirred for about 2 h. After the reaction, the solvent was removed under reduced pressure. The residue was dissolved in acetonitrile and filtered. Diethyl ether was added to the filtrate. After about 5 h, a red precipitate was formed and was collected and dried under vacuum. MS (ESI) m/e=about 606.50 ($M^-$). UV-Vis ($CH_2Cl_2$), λmax, nm ($M^{-1}$ $cm^{-1}$): about 454 (about 9100). Selected FT-IR absorption bands for the collected solid (KBr pellet, $\nu/cm^{-1}$): about 1591 ν(amide I); about 1492 ν(amide II). Analysis for $C_{38}H_{62}FeN_7O_4$: found, C about 61.92, H about 8.49, N about 12.27; calculated C about 61.95, H about 8.48, N about 13.31.

The reaction between $H_2$Bupdca and $FeCl_3$ is also performed without addition of base, similar to conditions used for the polymer network preparation, as described below: A solution of $FeCl_3 \cdot 6H_2O$ (about 135 mg, about 0.50 mmol) in about 1 mL of methanol was slowly added with stirring to a solution of $H_2$Bupdca (about 305 mg, about 1.10 mmol) in about 20 mL of methylene dichloride. The resulting deep orange solution was stirred for about 12 h at room temperature. Then the solution was evaporated under reduced pressure and the residue was washed with diethyl ether (about 3×50 mL) to afford about 245 mg (about 76%) of orange solid as product. Selected FT-IR absorption bands (KBr pellet, $\nu/cm^{-1}$): about 3278 ν(N—H); about 1635 ν(amide I); about 1539 ν(amide II). UV-Vis ($CH_2Cl_2$), λmax, nm ($M^{-1}$ $cm^{-1}$): about 361 (about 3300). MS (MALDI-TOF) m/e=about 608.83 ($M^+$). Analysis: found, C about 55.93, H about 6.85, N about 13.02; calculated for [Fe(HBupdca)$_2$]Cl ($C_{30}H_{43}FeN_6O_4$) C about 55.95, H about 6.89, N about 13.05; calculated for [Fe(HBupdca)(Bupdca)] ($C_{30}H_{43}FeN_6O_4$) C about 59.31, H about 7.13, N about 13.83.

The UV-Vis and FT-IR for the product from the reaction between $H_2$Bupdca and $FeCl_3$ without addition of base is different from ($Et_4N$)[Fe(Bupdca)$_2$]. The measured molecular mass is about 608.83 which indicates two possible complex structures (FIG. 10), Fe(HBupdca)(Bupdca) and [Fe(HBupdca)$_2$]$^+$. In Fe(HBupdca)(Bupdca), one of the $H_2$Bupdca is singly deprotonated while the other $H_2$Bupdca is double deprotonated. The Fe(III) ion is coordinated to these two Bu-pdca (denoted as HBupdca and Bupdca respectively), forming a neutral coordination complex. In [Fe(HBupdca)$_2$]$^+$, both ligands coordinating to Fe(III) are singly deprotonated, thus forming a cationic complex. Cl$^-$ was the counter ion. The complex of [Fe(HBupdca)$_2$]$^+$ was further validated by the following results: 1) addition of AgNO$_3$ to the solution of the product results in white AgCl precipitates, indicating that Cl$^-$ are presented in the coordination complex; and 2) the elemental analysis are in better agreement with [Fe(HBupdca)$_2$]$^+$ than with Fe(HBupdca)(Bupdca).

In [Fe(HBupdca)$_2$]$^+$, various coordination configurations are possible as both the N$_{amide}$ and O$_{amide}$ can be coordinated to Fe(III) ions. In order to determine the exact coordination configuration, the relative energy of different coordination modes and spin multiplicity is calculated. The calculations were performed with DFT method at unrestricted OPBE level as this method can be more accurate for predicting spin-state energies for iron complexes. The PDMS polymer was modeled as a —CH$_3$ group as it does not affect the energetic difference. LANL2DZ pseudo-potential was used for the Fe atom and the standard 6-31G(d) basis set for non-metallic atoms. Since Fe(III) has five 3d electrons, the complexed Fe(III) central atom can be in either low-spin (S=1/2), intermediate-spin (S=3/2), or high spin (S=5/2) state. Molecular structures with these spin states were fully optimized without any symmetry constraints. All the molecular properties were calculated at the same level of theory and using the Gaussian 09 program package. The results show that in the lowest energy structure, the Fe(III) is coordinated to two N atoms on the pyridine group, two N atoms on the deprotonated amide group, and two O atoms on the protonated group (FIG. 11). The resulting coordination complex is monocationic, with Cl$^-$ as the counter anion.

The bond energies were calculated from the bond-valence-bond-length correlation according to equation (1) and (2):

$$E=aS^2 \quad (1)$$

$$S=\exp((R_0-R)/b) \quad (2)$$

where a equals to about 7 eV vu$^{-2}$, R is the observed bond length, and R$_0$ and b are fitted bond valence parameters. R$_0$=about 1.815, b=about 0.37 for Fe(III)-N bond; R$_0$=about 1.759, b=about 0.37 for Fe(III)-O bond according the crystallographic data in literature and the optimized structure in the calculations. R=about 1.875, about 1.979 and about 2.014 Å for Fe—N$_{pyridine}$, Fe—N$_{amide}$, Fe—O$_{amide}$ bond, respectively. The calculated data for bond valence and bond energies are summarized in Table 1.

TABLE 1

Binding energies between Fe$^{3+}$ and N$_{pyridine}$, N$_{amide}$ and O$_{amide}$ atoms.

| Bond type | Bond length (Å) | Bond valence (v.u.) | Bond energy (Kcal/mol)$^b$ |
|---|---|---|---|
| Fe—N$_{pyridyl}$ | 1.875 | 0.948 | 145.0 |
| Fe—N$_{amido}$ | 1.979 | 0.716 | 87.7 |
| Fe—O$_{amido}$ | 2.014 | 0.502 | 40.7 |

This complex is unstable toward coordinating solvents. When dissolved in H$_2$O, DMF, DMSO, CH$_3$CN and CH$_3$OH, the shape and absorption peak of the UV-Vis spectra changed significantly, indicating that the complex was decomposed due to the coordination of Fe(III) with the solvent molecules (FIG. 12). These results indicate that the coordination between H-Bu-pdca and Fe(III) is quite weak, which is also evidenced by the FT-IR as the shifts in vN—H, vC=O are very insignificant. In contrast, the UV-Vis spectra of (Et$_4$N)[Fe(Bupdca)$_2$] in different solvents do not show significant changes except for typical solvatochromic shifts, indicating that this complex is stable in those solvents.

TABLE 2

Comparison of mechanical properties of polymer materials.

| | Young's modulus (MPa) | Maximal strength (MPa) | Breaking strength (MPa) | Breaking strain(mm mm$^{-1}$) |
|---|---|---|---|---|
| Fe-Hpdca-PDMS(1:1) | 0.81 | 0.52 | 0.52 | 570 |
| Fe-Hpdca-PDMS(1:2) | 0.54 | 0.23 | 0.23 | 1860 |
| Fe-Hpdca-PDMS(1:3) | 0.32 | 0.10 | 0.07 | 3890 |
| Fe-Hpdca-PDMS(1:4) | 0.23 | 0.06 | 0.05 | 5180 |
| Fe-Hpdca-PDMS(1:5) | 0.15 | 0.03 | 0.02 | 6150 |
| Fe-Hpdca-PDMS(1:6) | 0.09 | 0.04 | — | — |
| Fe-Hpdca-PDMS'(1:2) | 0.90 | 0.69 | 0.69 | 820 |
| Fe-Hpdca-PDMS"(1:2) | 0.08 | 0.03 | 0.02 | 1280 |

Sample size: about 75 × 14 × 1.0 mm$^3$;
Gage length: about 2 mm;
Stretching speed: about 10 mm min$^{-1}$.
Fe-Hpdca-PDMS, Fe-Hpdca-PDMS', and Fe-Hpdca-PDMS" were polymerized from H$_2$N-PDMS-NH$_2$ with Mn of about 5,000-7,000, about 2,500-4,000 and about 15,000-20,000, respectively.

As used herein, the singular terms "a," "an," and "the" may include plural referents unless the context clearly dictates otherwise. Thus, for example, reference to an object may include multiple objects unless the context clearly dictates otherwise.

As used herein, the terms "substantially" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can encompass a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

While this disclosure has been described with reference to the specific embodiments thereof, it should be understood by those skilled in the art that various changes may be made and equivalents may be substituted without departing from the true spirit and scope of this disclosure as defined by the appended claims. In addition, many modifications may be made to adapt a particular situation, material, composition of matter, method, operation or operations, to the objective, spirit and scope of this disclosure. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of this disclosure. Accordingly, unless specifically indicated herein, the order and grouping of the operations are not a limitation of this disclosure.

What is claimed is:

1. A self-healing polymer, comprising:
   metal ions; and
   a polymer network including polymer chains cross-linked through coordination bonds with the metal ions, wherein each polymer chain includes ligands within a backbone of the polymer chain, and the ligands include metal ion coordination sites, wherein at least one of the ligand is a poly-dentate ligand including multiple metal ion coordination sites having different bonding strength.

2. The self-healing polymer of claim 1, wherein the metal ions are selected from transition metal ions and metal ions of lanthanides.

3. The self-healing polymer of claim 1, wherein at least one of the ligands is a poly-dentate ligand, the poly-dentate ligand includes a first metal ion coordination site having a first bonding strength, a second metal ion coordination site having a second bonding strength, and a third metal ion coordination site having a third bonding strength, and the first bonding strength, the second bonding strength, and the third bonding strength are different.

4. The self-healing polymer of claim 3, wherein the first metal ion coordination site includes i) a nitrogen atom of a heteroaryl group or ii) a carboxylic acid group.

5. The self-healing polymer of claim 3, wherein the second metal ion coordination site includes a nitrogen atom of an amide group.

6. The self-healing polymer of claim 3, wherein the third metal ion coordination site includes an oxygen atom of an amide group.

7. The self-healing polymer of claim 1, wherein each polymer chain further includes a moiety selected from a polysiloxane chain, a polyamide chain, a polyisobutene chain, a polyolefin chain, a polyester chain, and a polyurethane chain.

8. The self-healing polymer of claim 1, wherein the self-healing polymer has a glass transition temperature no greater than 25° C.

9. The self-healing polymer of claim 8, wherein the glass transition temperature is in a range from −150° C. to 25° C.

10. The self-healing polymer of claim 1, wherein the self-healing polymer has a reversible elongation of at least 15× of an original length.

11. The self-healing polymer of claim 1, wherein a molar ratio of the poly-dentate ligand to the metal ions is in a range from 1:10 to 10:1.

12. An actuator, comprising:
    a first electrode;
    a second electrode; and
    an elastomeric film connected to the first electrode and the second electrode, wherein the elastomeric film includes the self-healing polymer of claim 1.

* * * * *